(12) United States Patent
Corbett et al.

(10) Patent No.: US 8,880,356 B2
(45) Date of Patent: Nov. 4, 2014

(54) METHOD AND SYSTEM FOR SPECTRUM DATA ANALYSIS

(75) Inventors: Daniel Roy Corbett, Pullenvale (AU); Paul Gottlieb, West End (AU); Andrew Harley Menzies, Region II (CL); Michael James Owen, Geebung (AU)

(73) Assignee: Fei Company, Hillsboro, OR (US)

( * ) Notice: Subject to any disclaimer, the term of this patent is extended or adjusted under 35 U.S.C. 154(b) by 755 days.

(21) Appl. No.: 12/866,697

(22) PCT Filed: Feb. 6, 2009

(86) PCT No.: PCT/US2009/033493
§ 371 (c)(1),
(2), (4) Date: Feb. 25, 2011

(87) PCT Pub. No.: WO2009/100404
PCT Pub. Date: Aug. 13, 2009

(65) Prior Publication Data
US 2011/0144922 A1    Jun. 16, 2011

(30) Foreign Application Priority Data
Feb. 6, 2008    (AU) .............................. 2008900546

(51) Int. Cl.
*G01N 23/00*    (2006.01)
*G01N 23/207*    (2006.01)
*H01J 37/28*    (2006.01)

(52) U.S. Cl.
CPC ............ *G01N 23/2076* (2013.01); *H01J 37/28* (2013.01)
USPC .............................. 702/28; 250/307; 250/310

(58) Field of Classification Search
USPC ........ 378/45; 702/28; 250/305, 307, 310, 703
See application file for complete search history.

(56) References Cited

U.S. PATENT DOCUMENTS

| | | | |
|---|---|---|---|
| 4,037,101 A | | 7/1977 | Okumura et al. |
| 4,476,386 A | * | 10/1984 | Reid et al. ..................... 250/310 |
| 4,592,082 A | | 5/1986 | Pawloski |

(Continued)

FOREIGN PATENT DOCUMENTS

| | | |
|---|---|---|
| CN | 100498309 | 6/2009 |
| JP | 08015185 | 1/1996 |

(Continued)

OTHER PUBLICATIONS

B. Vekemans et al, Analysis of x-ray Spectra by Iterative Least Square (AXIL): New Developments, May 30-Jun. 3, 1994, John Wiley and Son Ltd., vol. 23, pp. 278-285.*

(Continued)

*Primary Examiner* — John Breene
*Assistant Examiner* — Eman Alkafawi
(74) *Attorney, Agent, or Firm* — Scheinberg & Associates, PC; Michael O. Scheinberg; John Horvath

(57) ABSTRACT

A method and system for spectrum data analysis. The method comprises the steps of collecting a spectrum of an unknown material; providing a set of data templates; calculating weighting factors for the element data templates to minimize error in approximating the spectrum; removing one or more of the templates having negative weights in approximating the spectrum; and re-calculating an approximation of the spectrum with said one or more templates removed. Embodiments of the invention are suitable for analyzing noisy spectra having relatively few data points.

22 Claims, 25 Drawing Sheets

(56) References Cited

U.S. PATENT DOCUMENTS

| | | | |
|---|---|---|---|
| 4,807,148 | A | 2/1989 | Lacey |
| 4,839,516 | A | 6/1989 | Freeman et al. |
| 5,555,198 | A | 9/1996 | Asano |
| 5,741,707 | A | 4/1998 | Herron et al. |
| 5,798,525 | A | 8/1998 | Benizri-Carl et al. |
| 5,866,903 | A * | 2/1999 | Morita et al. ............... 250/310 |
| 5,906,919 | A | 5/1999 | Garini et al. |
| 5,991,028 | A | 11/1999 | Cabib et al. |
| 6,018,587 | A | 1/2000 | Cabib |
| 6,066,459 | A | 5/2000 | Garini et al. |
| 6,122,343 | A | 9/2000 | Pidcock |
| 6,282,301 | B1 | 8/2001 | Haskett |
| 6,341,257 | B1 | 1/2002 | Haaland |
| 6,377,652 | B1 | 4/2002 | Sturm |
| 6,385,281 | B1 | 5/2002 | Ozawa et al. |
| 6,466,929 | B1 | 10/2002 | Brown et al. |
| 6,470,335 | B1 | 10/2002 | Marusak |
| 6,584,413 | B1 * | 6/2003 | Keenan et al. ............... 702/28 |
| 6,658,143 | B2 | 12/2003 | Hansen et al. |
| 6,674,894 | B1 | 1/2004 | Parker et al. |
| 6,687,620 | B1 | 2/2004 | Haaland et al. |
| 6,711,503 | B2 | 3/2004 | Haaland |
| 6,724,940 | B1 | 4/2004 | Qian et al. |
| 6,765,205 | B2 * | 7/2004 | Ochiai et al. ............... 850/9 |
| 6,842,702 | B2 | 1/2005 | Haaland et al. |
| 6,993,170 | B2 | 1/2006 | Johnson et al. |
| 7,139,415 | B2 | 11/2006 | Finkbeiner |
| 7,161,672 | B2 | 1/2007 | Gornushkin et al. |
| 7,243,030 | B2 | 7/2007 | Reeve et al. |
| 7,400,770 | B2 | 7/2008 | Keaton et al. |
| 7,436,510 | B2 | 10/2008 | Grun et al. |
| 7,790,465 | B2 | 9/2010 | Otvos |
| 2002/0169589 | A1 | 11/2002 | Banki et al. |
| 2004/0027350 | A1 | 2/2004 | Kincaid et al. |
| 2004/0147830 | A1 | 7/2004 | Parker et al. |
| 2005/0037515 | A1 | 2/2005 | Nicholson et al. |
| 2006/0028643 | A1 * | 2/2006 | Gottlieb et al. ............... 356/300 |
| 2006/0291619 | A1 * | 12/2006 | Statham ............... 378/45 |
| 2008/0137082 | A1 | 6/2008 | Grun et al. |

FOREIGN PATENT DOCUMENTS

| | | |
|---|---|---|
| JP | 2000-249668 | 9/2000 |
| JP | 2001-066269 | 3/2001 |
| RU | 2054660 | 2/1996 |
| WO | 9905503 | 2/1999 |

OTHER PUBLICATIONS

Meyer, K., et al., 'Qualitative and Quantitative Mixture Analysis by Library Search: Infrared Analysis of Mixtures of Carbohydrates,' Analytica Chimica Acta, Sep. 1, 1993, pp. 161-171, vol. 161-171.

Sutherland, David N., "Image Analysis for Off-Line Characterisation of Mineral Particles and Prediction of Processing Properties," Part. Part. Syst. Charact., 1993, pp. 271-274, vol. 10.

Benz, Ursula C. et al., "Multi-resolution, Object-oriented Fuzzy Analysis of Remote Sensing Data for GIS-ready Information," ISPRS Journal of Photogrammetry & Remote Sensing, 2004, pp. 239-258, vol. 58.

Creelman, Robert A. et al., "A Scanning Electron Microscope Method for Automated, Quantitative Analysis of Mineral Matter in Coal," International Journal of Coal Geology, 1996, pp. 249-269, vol. 30.

Gottlieb, P. et al., "The Automatic Identification and Quantification of Silver Minerals," XVIII International Mineral Processing Congress, May 23-28, 1993, pp. 475-481, Sydney, Australia.

Gottlieb, P. et al., "Using Quantitative Electron Microscopy for Process Mineralogy Applications," Microtextural Mineralogy, Apr. 2000, pp. 24-25.

Hazel, Geoffrey G., "Object-level Processing of Spectral Imagery for Detection of Targets and Changes Using Spatial-Spectral-Temporal Techniques," Proceeding of the SPIE, 2001, pp. 380-390, vol. 4381.

Newbury, Dale E., "Chemical Compositional Mapping by Microbeam Analysis at the Micrometer Scale and Finer," Microelectronics Journal, 1997. pp. 489-508, vol. 28.

Sutherland, D.N. et al., "Application of Automated Quantitative Mineralogy in Mineral Processing," Minerals Engineering, 1991, pp. 753-762, vol. 4, Nos. 7-11.

Ghassemian, Hassan et al., "Object-Oriented Feature Extraction Method for Image Data Compaction," IEEE Control Systems Magazine, Jun. 1998, pp. 42-48.

Ashton, Edward A. et al., "Multialgorithm Solution for Automated Multispectral Target Detection," Opt. Eng., Apr. 1999, pp. 717-724, vol. 38, No. 4.

Kern, Denise, J. et al., 'Two sub-states of the red2 state of methyl-coenzyme M reductase revealed by high-field EPR spectroscopy,' J. Biol. Inorg. Chem., Aug. 10, 2007, pp. 1097-1105, vol. 12, No. 8.

Tellinghuizen, Joel, 'On the Role of Statistical Weighting in the Least-Squares Analysis of UV-Visible Spectrophotometric Data,' Applied Spectroscopy, Aug. 1, 2000, pp. 1208-1213, vol. 54, No. 8.

* cited by examiner

High Level Iterative Least Squares Algorithm

Background element substitution algorithm

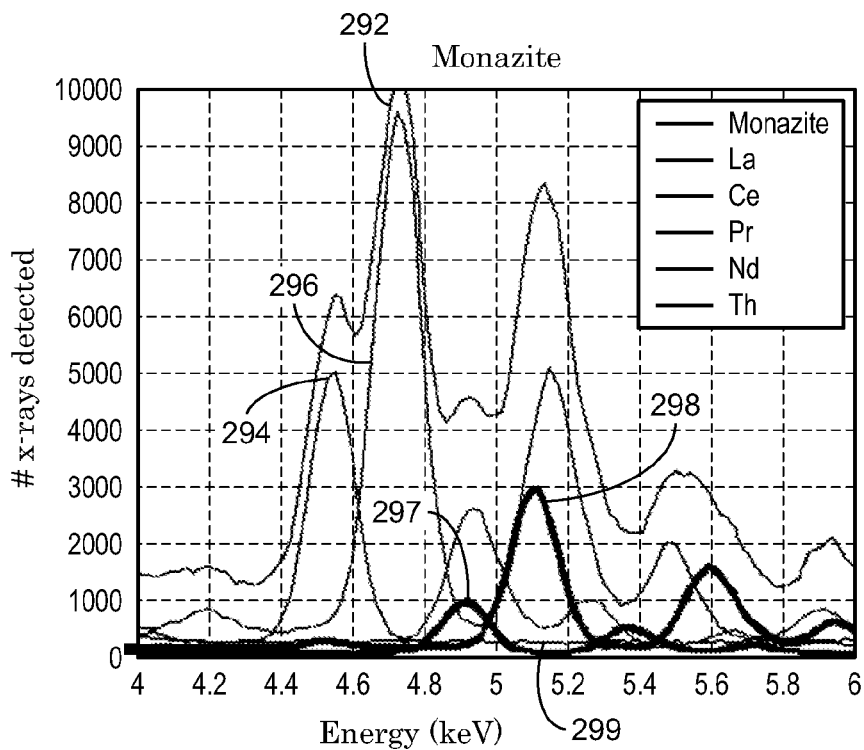
FIG. 29: Monazite
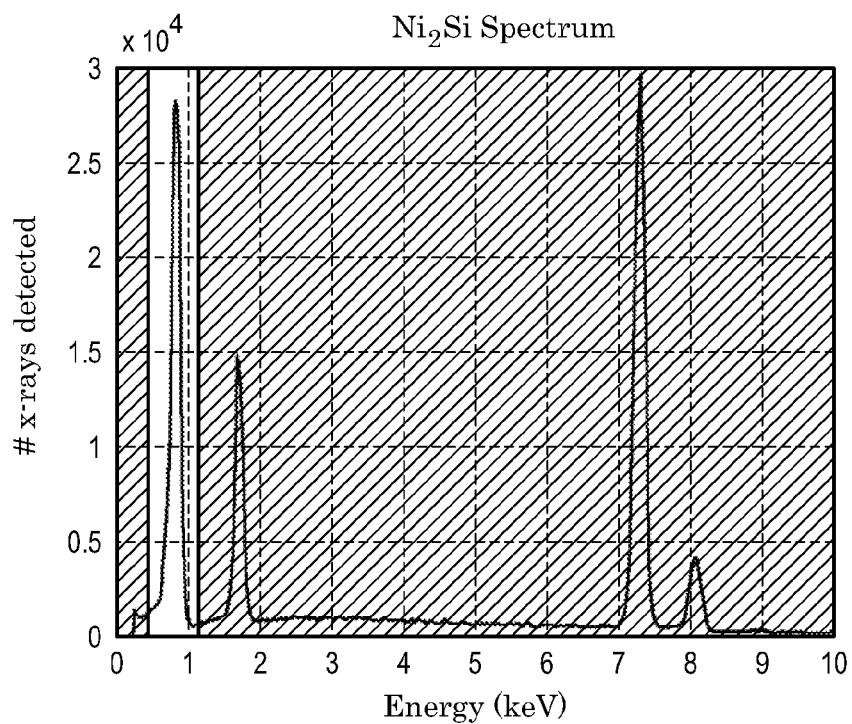
FIG. 30

METHOD AND SYSTEM FOR SPECTRUM DATA ANALYSIS

FIELD OF INVENTION

The present invention relates broadly to a method and system for spectrum data analysis

BACKGROUND

In many applications, information about a sample is determined by accumulating radiation from the sample over a period of time. A characteristic of the radiation, such as its energy profile or its diffraction pattern, can often be correlated to the type of material present in the sample. For example, when bombarded by electrons, a sample gives off characteristic x-rays whose energy correlates to the elements in the sample. Similarly, when bombarded with x-rays, crystals produce a characteristic diffraction pattern, and the frequency spectrum of gamma rays and other radiation are used by astronomers to learn about the composition of universe. The term "sample" is used broadly herein to include an object under observation.

In one widely used application, a scanning electron microscope can be used to determine the elemental composition of an unknown material. The scanning electron microscope (SEM) sends high-energy electrons smashing into material. When these electrons enter an atom, they can knock electrons out of the material. In the process, the first electron looses some energy, but can go on to smash into other atoms until it no longer has enough energy to continue doing so.

FIG. 1 shows an atom with electrons bound to the K, L, and M energy levels. An electron from the SEM is fired into this atom at a very high energy, dislodging one of the electrons from the atom. A very short time later, an electron from a higher energy level will fall into the created gap. In the process of falling into the lower energy K shell, it emits a single x-ray to balance the overall energy. The energy of the emitted x-ray depends on the initial location of the electron. If the electron originates from the L shell, then the radiation is designated as K$\alpha$ radiation. If it originates from the M shell, then the radiation is designated as K$\beta$ radiation, which has a higher energy than K$\alpha$ radiation.

Alternatively, if an electron was dislodged from the L energy level, then a different set of x-rays may be omitted, depending from where the electron that will fill in the emptied position originates. FIG. 1 shows that an electron falling from the M shell to the L shell is associated with the emission of L$\alpha$ a radiation.

The emitted x-rays are dependent on the specific starting and finishing energy levels. By analyzing the energy of the emitted x-ray, the type of the emitting atom can be determined. Each element in the periodic table has a specific set of energies corresponding to these x-ray energies. For example, the energy of the K$\alpha$ radiation for carbon is 277 eV, compared to 523 eV for oxygen, or 98434 eV for uranium. If the electron from the SEM has a lower energy than this binding energy, then it is unable to dislodge the electron from the atom.

A complete list of binding energies for each element can be seen at http://xdb.lbl.gov/Section1/Table_1-2.pdf.

Alternatively, the electrons from the SEM may not enter an atom, but may be deflected away from an atom. This is caused by the negative electric charge on the electron being repelled by the negative charge of the electron cloud around the atoms.

FIG. 2 shows that the path of the electron is deflected away from an atom due to mutual electrostatic repulsion. The deflection of the path causes a small drop in energy of the high energy electron. This generates the Bremsstrahlung radiation. This effect occurs at lower intensities than the emission of x-rays seen in FIG. 1. However, it also occurs at all energy levels, rather than at discrete energy levels. The Bremsstrahlung radiation is an artefact of using an electron beam from a SEM. It must be taken into account when calculating the elemental composition. The shape of the Bremsstrahlung radiation depends on the average density of the material being analyzed, and is also affected by the standard based spectral analysis.

Standard Based Spectral Analysis

Standard based spectral analysis is a term used to describe the process of comparing the spectrum of an unknown mineral or element with a set of known spectra to determine the composition of the unknown spectrum in terms of the known spectra. This approach generates a solution that represents a multiplication factor for each of the known templates, which are then added together to synthesize the unknown spectrum.

FIG. 3 shows the spectrum of pyrite ($FeS_2$). The spectrum comprises several peaks, and some regions of Bremsstrahlung radiation. There are some additional smaller peaks in this plot that are due to carbon (at 277 eV), and the iron L$\alpha$ peak at 705 eV.

If one measures a sample of pure iron and pure sulphur, the spectra of these elements can be overlaid onto the spectrum of pyrite appropriately. The result is shown in FIG. 4. In particular, FIG. 4 shows that scaling the iron spectrum 44 to 42.0% and the sulphur spectrum 46 to 41.5% allows them to fit the peaks in the pyrite spectrum 42. These numbers are the peak ratios of these elements, because they represent the ratio of the area of each peak relative to a pure sample of the element. They do not represent the weight percentage of the material.

Matrix Corrections

The peak ratios obtained previously can be converted to a weight percentage using a standard matrix correction algorithm such as ZAF corrections. ZAF corrections account for differences in the atomic number (Z) of the elements, the absorption factor (A) of x-rays travelling through the material, and fluorescence (F) of x-rays from elements stimulating the emission of x-rays from other elements.

Issues with Standards-Based Spectral Analysis

In order to use standard-based spectral analysis, the operating conditions of the SEM must be determined. The factors that influence spectral analysis are the beam voltage, x-ray detector angles and beam current. The beam voltage affects the peaks that are stimulated and produce x-rays. As discussed previously in the text, if the beam voltage is lower than a particular binding energy for an elemental peak, then the peak is not present in the spectrum. In addition, the peaks that have a significantly lower binding energy are stimulated far more than peaks with binding energy close to the beam voltage. This results in the spectrum containing very large peaks in the low energy range, and very small peaks in the high energy range.

The x-ray detector angle affects the calculations for ZAF corrections, because it models the length of the path that the x-rays traverse through the material before reaching the detector.

The beam current affects the rate at which x-rays are generated. The standards need to be collected at the same current as the analysis is performed.

Overlapping Spectra

Some elemental spectra have peaks that overlap other element peaks. For instance, sulphur, lead and molybdenum have a peak at 2307 eV, 2342 eV and 2293 eV respectively. The elements have other peaks at different energies, but these spectra look very similar because the SEM beam voltage is too low to excite the molybdenum K peaks significantly (at 17481 eV). In addition, the lead K peaks are not excited at all because their energy is too high (74989 eV). This causes difficulties trying to resolve minerals that contain lead, sulphur or molybdenum. This is particularly difficult for galena which contains both lead and sulphur.

FIG. 5 shows the spectrum 52 for galena, and the scaled spectra 54 for lead and sulfur 56. The peaks for lead and sulfur overlap significantly, which makes the analysis of galena more difficult than pyrite. There are other elements whose elemental peaks overlap strongly and, thus, elemental artefacts may occur if one of these elements is present in the mineral. FIGS. 6 to 12 show further examples of such overlapping elements.

In particular, FIG. 7 shows that the platinum spectrum 74 and the zirconium spectrum 72 have an overlapping peak at 2.04 keV (channel 102). This causes problems in the analysis because it can incorrectly introduce zirconium to the analyzed composition if platinum is present. FIG. 8 shows the same type of overlapping peaks for the sodium spectrum 82 and the zinc spectrum 84. This causes sodium artefacts to be reported in minerals containing zinc. FIG. 9 shows that this type of overlap is also present for the aluminium spectrum 92 and the bromine spectrum 94. FIG. 10 shows the overlapping peak of the cadmium spectrum 102 and the uranium spectrum 104, which are very similar and could be confused at low concentration.

FIG. 11 shows the close overlap of the peaks of the silver spectrum 112 and the thorium spectrum 114. This close overlap causes problems at low count because the only difference between the spectra of these elements is the small peak at channel 648, which is invisible for low count spectra. This causes the identification of minerals containing either thorium or silver to incorrectly include the other element because of this overlap. Finally, FIG. 12 shows the overlapping peaks of the Yttrium spectrum 122 and the Iridium spectrum 124. Even such a relatively small overlap seems to cause problems for zirconia.

Low Count Spectral Analysis

The calculation of the constituent elements from a spectrum is not particularly difficult if high count spectra are used. For instance, FIG. 13 shows the spectrum of the mineral Albite ($NaAlSi_3O_8$) with the peaks shown very smoothly. The total number of x-rays collected to generate this spectrum was one million. In contrast, FIG. 14 shows the same mineral where the total number of x-rays collected was three hundred. In this figure, the jagged plot 142 shows the spectrum of the mineral, while the smooth plot 144 shows a fit of elemental spectra to the mineral. In the second example there is significant noise in the spectra and the peaks are not smooth. The elements reported for the low count spectra contain a number of artefacts that appear to be present based on the spectra, but are not present in the mineral. The task of analyzing spectra at low counts is more difficult because there is far more variability in the underlying spectrum, and the peaks of each element are not Gaussian. Therefore, the techniques used by existing approaches are unsuitable for low count spectral analysis for mineral identification, because they generally assume a smooth spectrum.

On the other hand, the accuracy of element quantification is lower for low-count spectra. If the elements shown in FIG. 13 and FIG. 14 are compared, it is apparent that the quantities of the four elements O, Na, Al and Si are slightly inaccurate at 300 counts.

SUMMARY

It is an object of the present invention to substantially overcome, or at least ameliorate, one or more disadvantages of existing arrangements; or to provide a useful alternative.

According to a first aspect of the present disclosure, there is provided a method for spectrum data analysis, the method comprising the steps of:
  collecting a spectrum of an unknown material;
  providing a set of element data templates;
  calculate optical least squares weights for the element data templates in approximating the spectrum;
  removing one or more of the templates having negative weights in approximating the spectrum; and
  re-calculating an approximation of the spectrum with said one or more templates removed.

According to a second aspect of the present disclosure, there is provided an electronic system for spectrum data analysis, the system comprising:
  spectrum acquisition means for obtaining an x-ray spectrum of an unknown material;
  memory means for storing a set of element data templates; and
  processing means for;
  calculating least squares weights for the element data templates in approximating the obtained spectrum;
  removing one or more of the templates having negative weights in approximating the spectrum; and
  re-calculating an approximation of the spectrum with said one or more templates removed.

According to another aspect of the present disclosure there is provided a computer program product including a computer readable medium having recorded thereon a computer program for implementing the aforementioned method.

Other aspects of the invention are also disclosed.

BRIEF DESCRIPTION OF THE DRAWINGS

Some conceptual diagrams and at least one embodiment of the present invention will now be described with reference to the drawings and appendices, in which:

FIG. 29 shows monazite.

FIG. 30 shows portions of the spectrum used to calculate the nickel K peak ratio.

DETAILED DESCRIPTION

Figure 1:
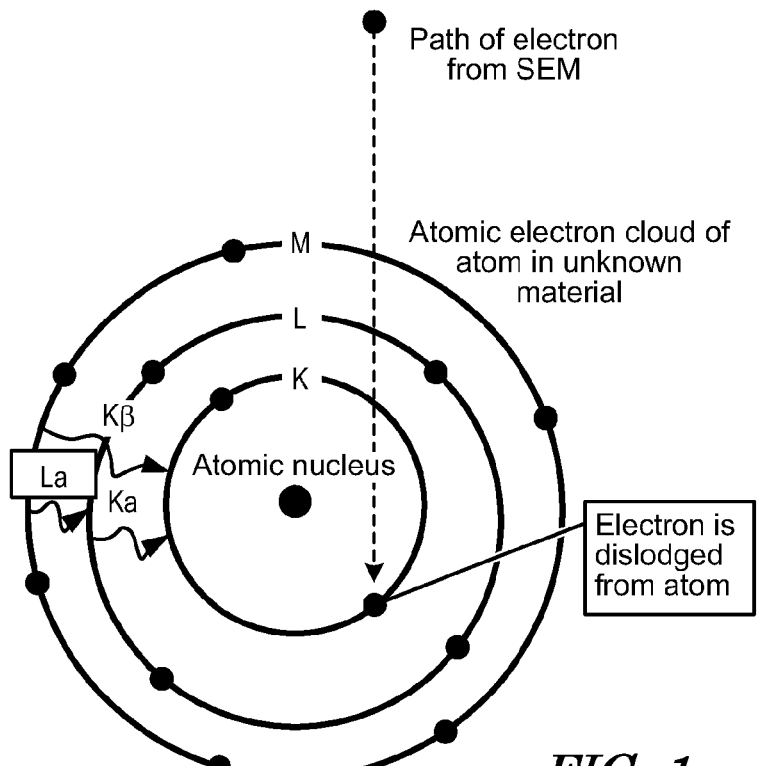
FIGS. 1 and 2 show conceptual energy diagrams and in principal functionality behind the method of standard electron microscopy (SEM).
Figure 2:
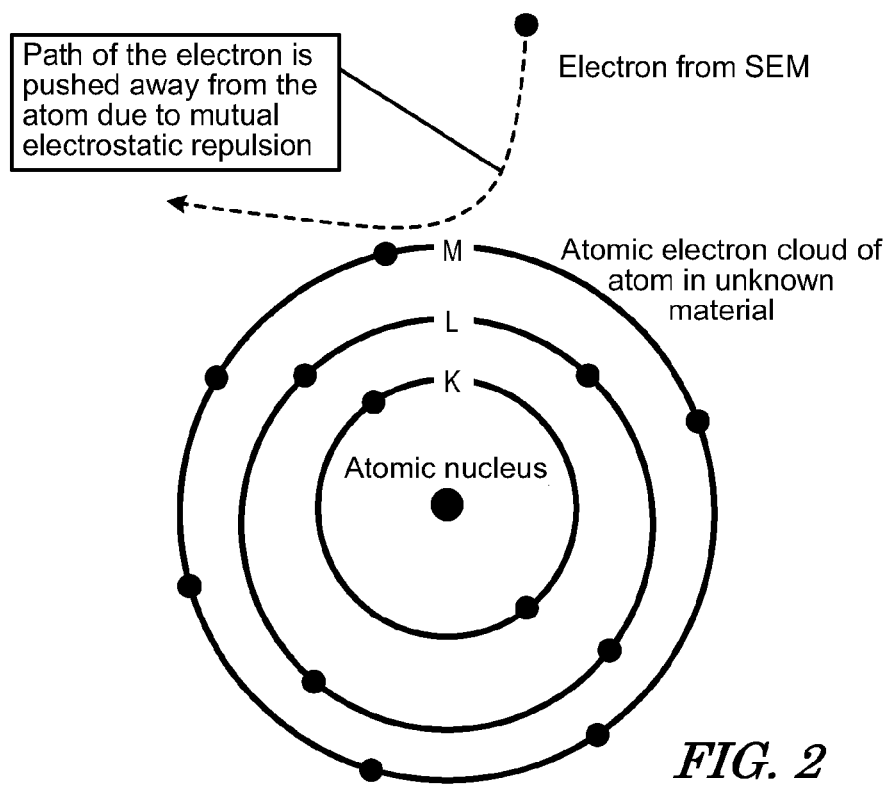
Figure 3:
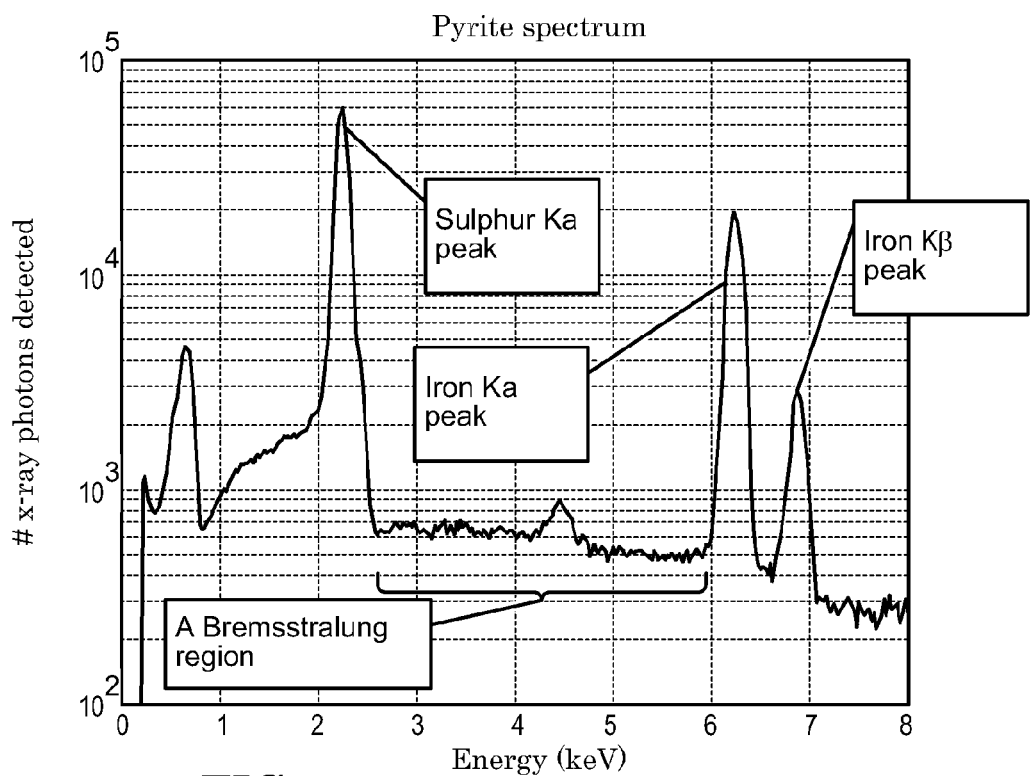
FIG. 3 shows the spectrum of mineral pyrite.

Embodiments of the invention are particularly well suited for determining sample characteristics using a relatively small number of "counts," that is, a relatively small amount of detected radiation. The radiation can be, for example, an x-ray spectrum for an electron microscope, an x-ray spectrum from X-ray fluorescence, an x-ray diffraction pattern, a light, microwave, or gamma ray spectra from an astronomical object, or a mass spectrum from a mass spectrometer. While the prior art interprets a smooth spectrum produced by a large number of counts, embodiments of the invention are suitable for determining materials from a rough, noisy spectrum having, for example, fewer than 100,000 counts, fewer than 10,000 counts, fewer than 1,000 counts, or fewer than 500 counts. Because it takes time to accumulate counts, embodiments of the invention allow for more rapid characterization of materials compared to the prior art. Embodiments of the invention can be used to determine, for example, the elemental composition of a sample in an x-ray spectroscopy embodiment, the mineral composition of a sample in an x-ray diffraction embodiment, or the mass composition of a sample, in a mass spectroscopy embodiment.

In an embodiment in which the invention is used to determine the elemental composition of a sample using x-ray spectroscopy, the standard operating conditions of the SEM configuration used in obtaining at least some of the results presented in the present description include 25 keV beam voltage, 5 nA beam current, and 35 degree x-ray detector angle. The beam voltage is too low to dislodge the electrons for uranium in the K shell, which require nearly four times that energy. However, it is high enough to dislodge the M shell electrons for uranium because they require 3165 eV.

Some portions of the description which follows are explicitly or implicitly presented in terms of algorithms and functional or symbolic representations of operations on data within a processor or a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

Thus, the present specification discloses both a method and an apparatus for performing the operations of the method. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Embodiments of the invention use one or more mathematical algorithms to approximate a measured property, such as an x-ray spectrograph, by using known data templates corresponding to various materials, and weighting factors that correlate to the relative abundance of those materials in the sample. Weighting factors are determined that produce, in combination with the data templates, a spectrum, diffraction pattern, or other pattern, that closely matches the measured pattern. The difference between the measured pattern and the combination of the data templates and weighting factors, is referred to an error value. Mathematical algorithms are used to minimize the error value. One preferred algorithm to find weighting factors that minimize the error value is an iterative least squares method, and is described in detail below. The invention is not limited to any particular algorithm.

Iterative Least Squares Algorithm

The iterative least squares analysis is a technique which uses standard linear least squares curve fitting to find the optimal weights for each template in order to synthesise the spectrum of an unknown material. It builds a list of candidate elements and uses various conditions to detect which elements are artefacts and which elements are in the solution.

Figure 15:
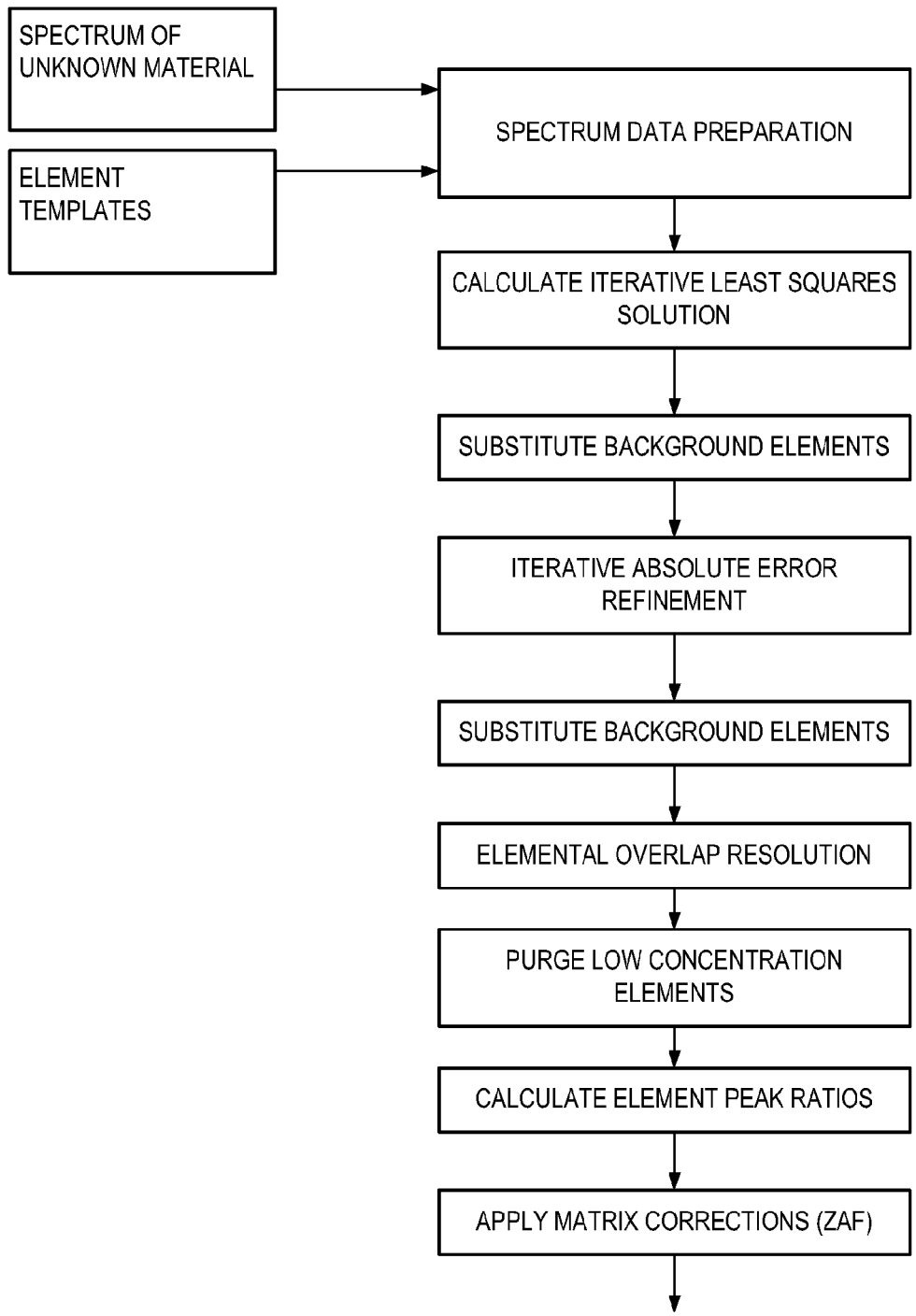
FIG. 15 shows a high-level flow diagram of the currently described Itterative Least Square Algorithm.

The spectral analysis algorithm disclosed here is presented in FIG. 15. The algorithm is directed at analysing low-count spectra (typically 1000 counts), but can also be applied for analysing high count spectra. It performs element identification and quantification simultaneously to compute the peak ratios of each element. It also applies real-world knowledge to address various minor deficiencies and to minimize the chance of reporting artefact elements that appear to be in the spectrum but are not actually present.

Spectrum Data preparation

Figure 4:
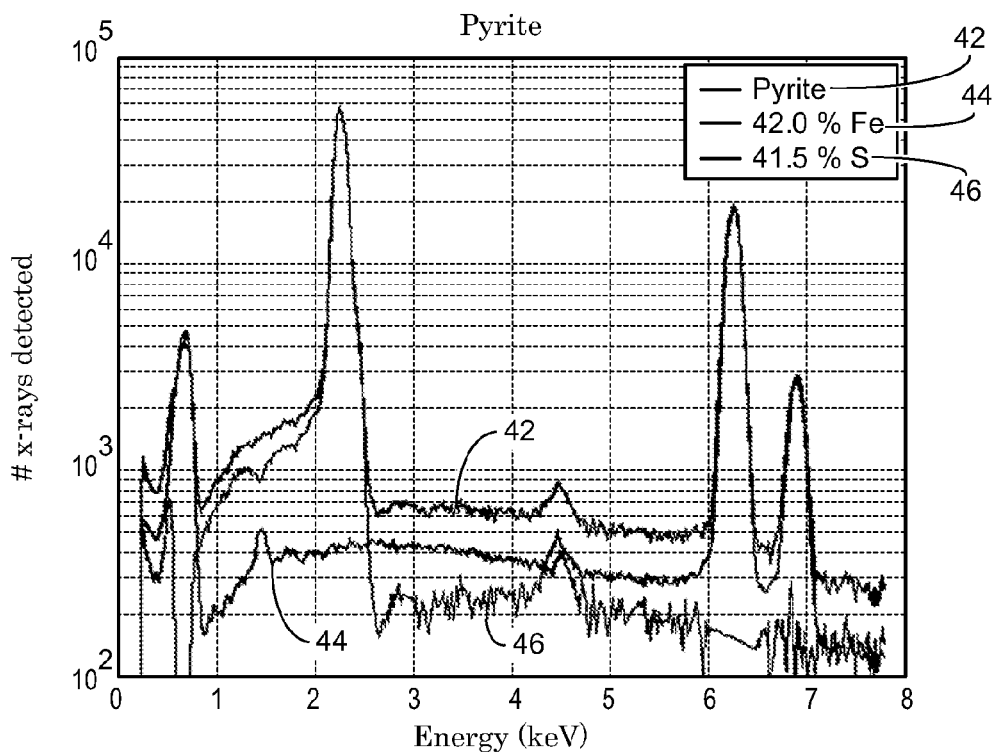
FIG. 4 shows a two-element spectral analysis of pyrite.
Figure 5:
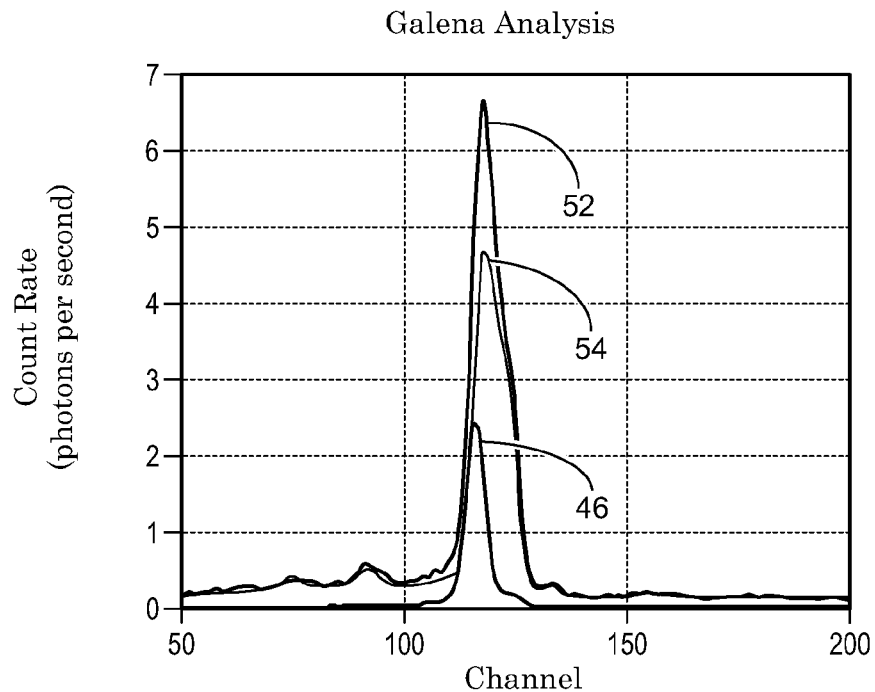
FIG. 5 shows the spectrum of Galena with nearby elements.
Figure 6:
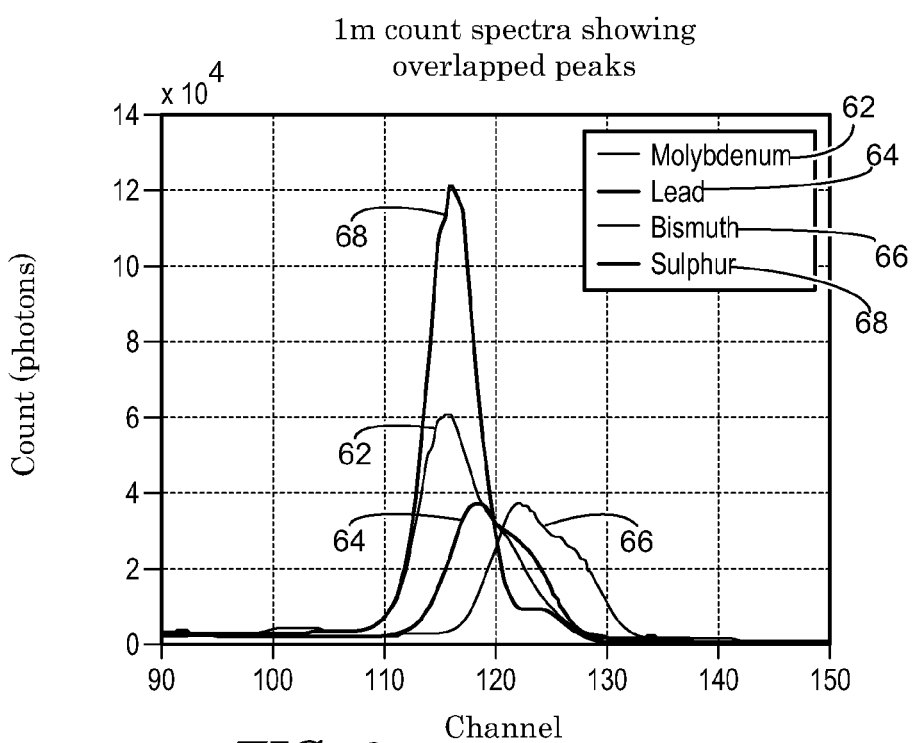
FIG. 6 illustrates the concept of element peak overlap.
Figure 7:
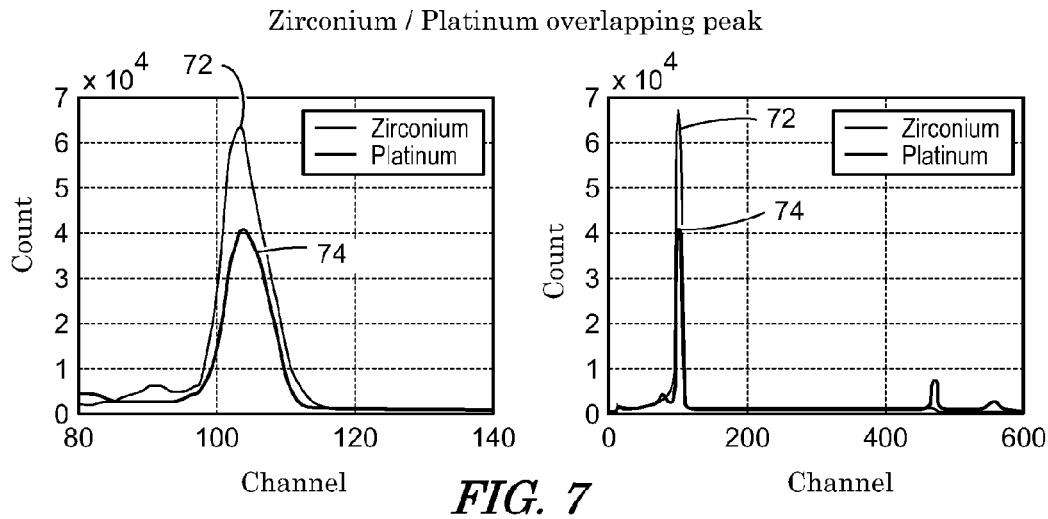
FIGS. 7 to 12 show the overlapping peaks of various elements.
Figure 8:
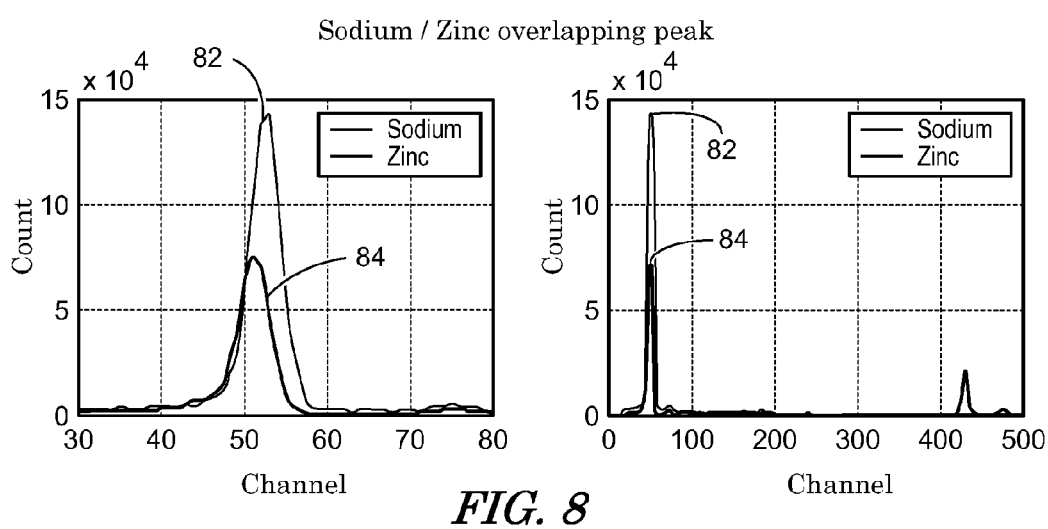
Figure 9:
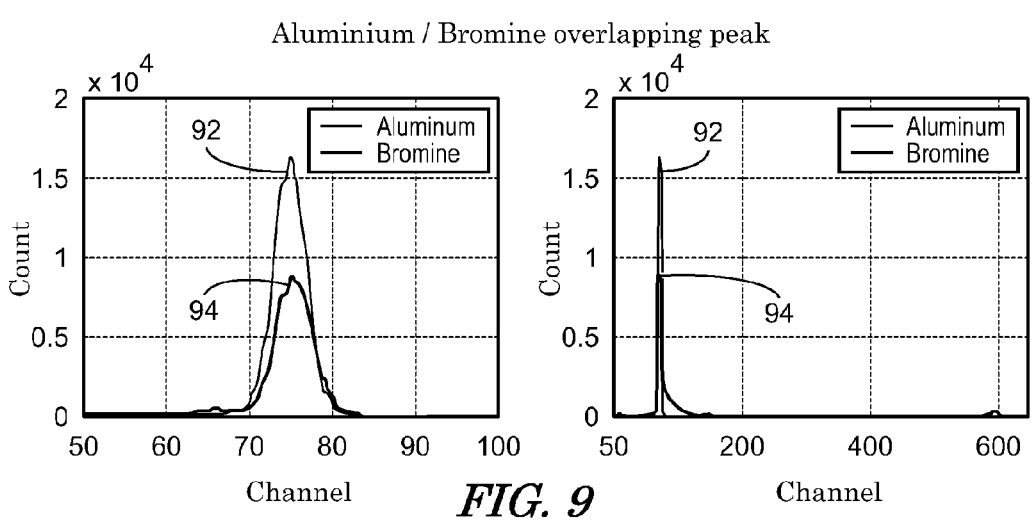
Figure 10:
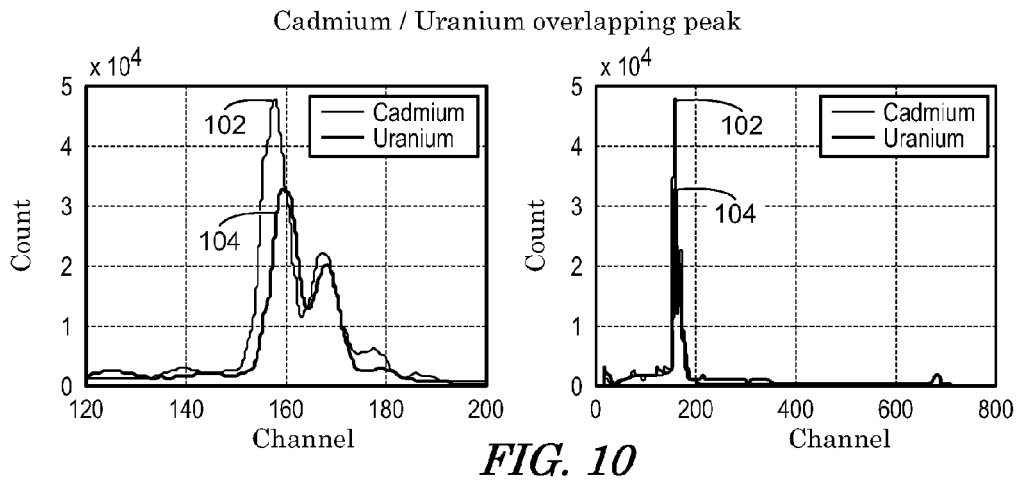
Figure 11:
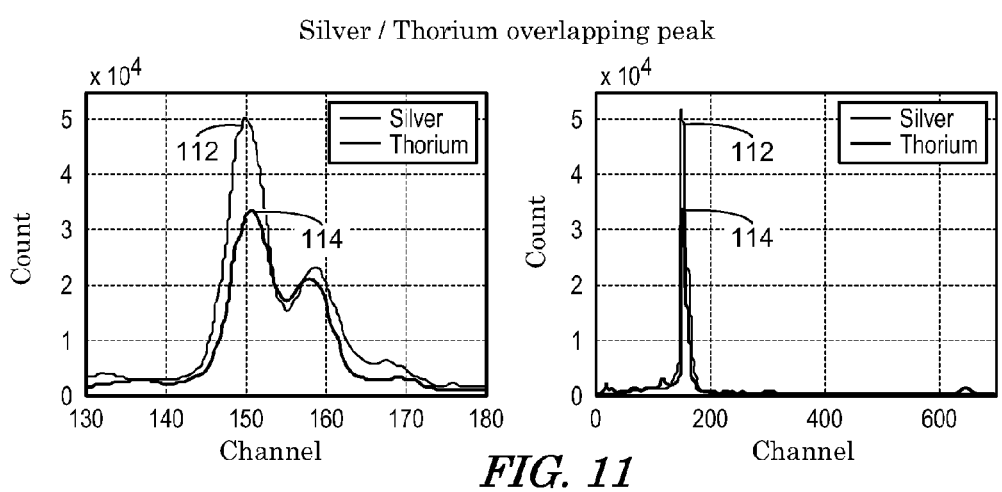
Figure 12:
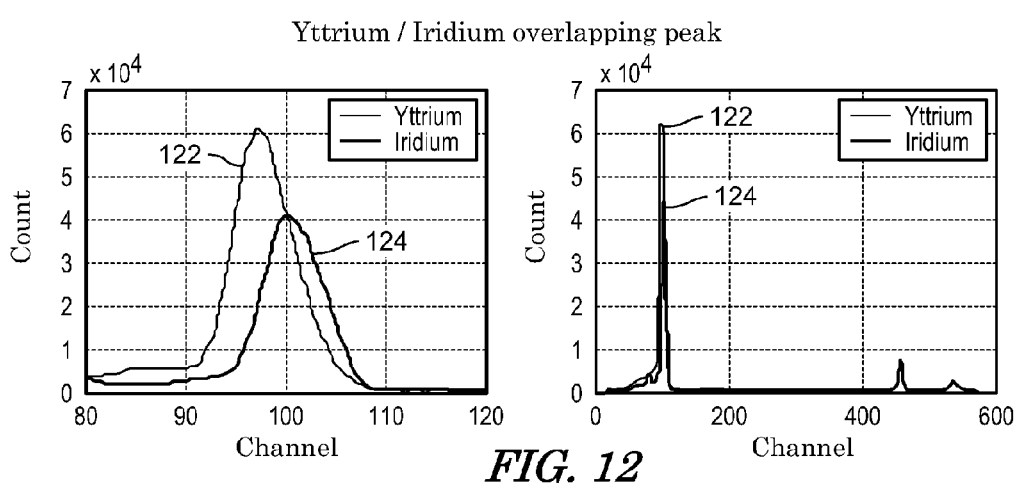
Figure 13:
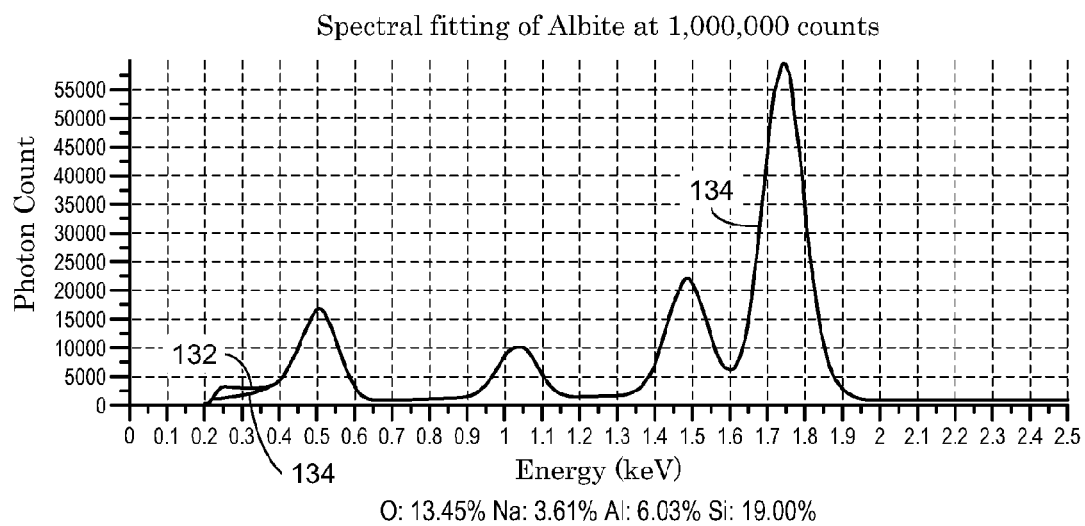
FIGS. 13 and 14 show two spectra of Albite obtained on the basis of different count number.
Figure 14:
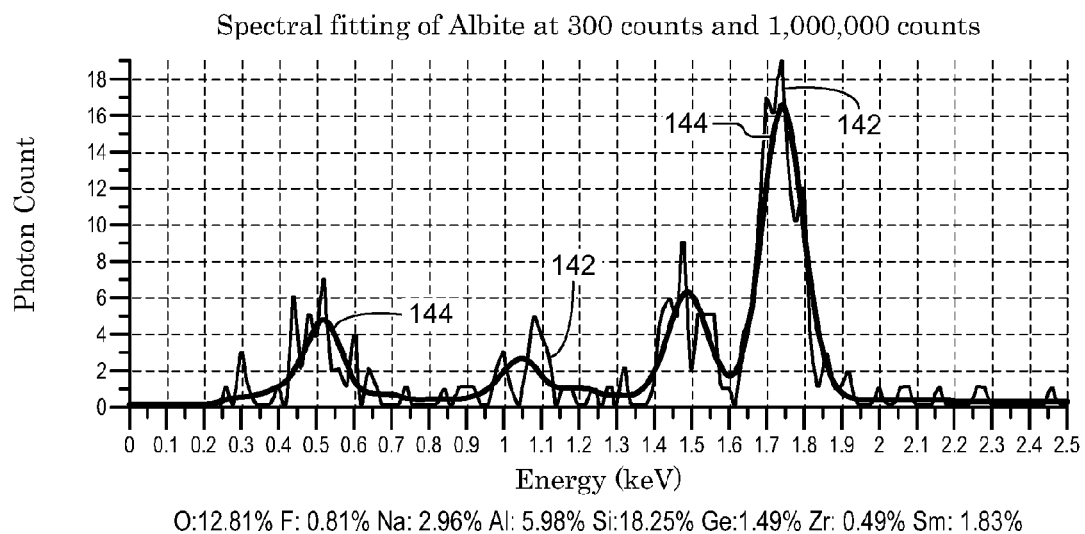

The raw spectrum data is altered to improve the discrimination ability between similar elements. When spectrum data is acquired, the data tends to have larger peaks at lower energy, and if any peaks are present at high energy they are generally far smaller in magnitude. This presents a problem for discriminating between similar elements (see FIG. 4 for example).

Non Uniform Spectra Sub-Sampling

In the non-uniform spectra sub-sampling phase, the spectrum is sub-sampled non uniformly. Such sampling preserves the resolution of the low energy portion of the spectrum, while increasing the peak signal-to-noise ratio at high energy at the expense of peak resolution. This trade-off is acceptable for two reasons—firstly the tiny high energy peaks become more important, and secondly the Energy-Dispersive Spectroscopy (EDS) x-ray detector has a resolution that is significantly worse at high energy compared to low energy.

The non-uniform sub-sampling is implemented as follows:

1. Retain the original spectrum for all channels below 8 keV. The purpose is to preserve the high resolution obtained by the x-ray detector for these channels. It also fits with the fact that elements have a higher count rate (i.e. rate at which x-rays are generated) at lower energy compared to higher energy. This arbitrary threshold was selected based on the spectra of nickel and copper, where the K-L ratio changes from greater-than-1 for nickel to a value of less-than-1 for copper. The copper K-alpha peak occurs at 8040 eV, and will be magnified accordingly.

Figure 16:
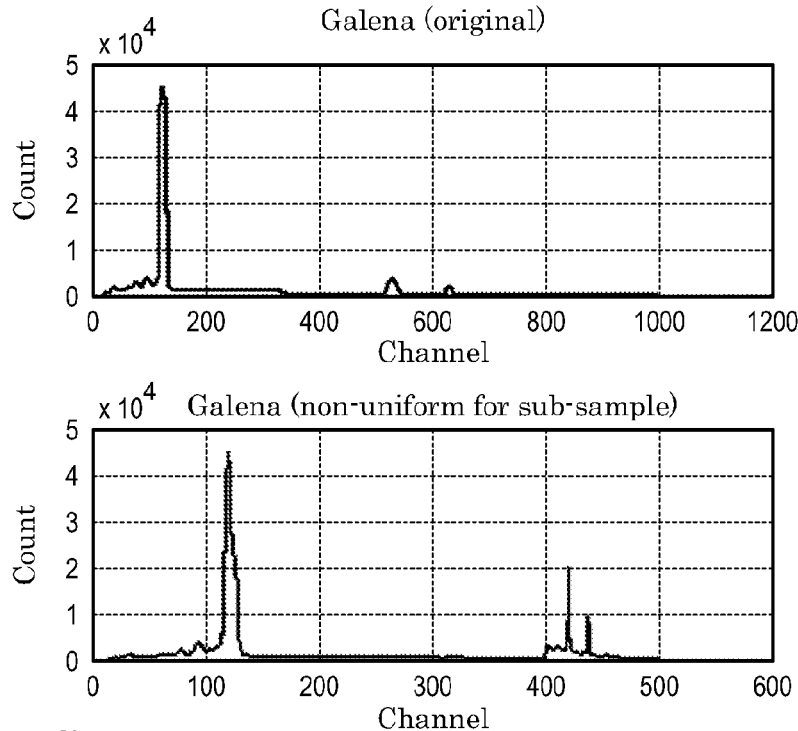
FIG. 16 shows galena(PbS) before and after non uniform sub-sampling.
Figure 17:
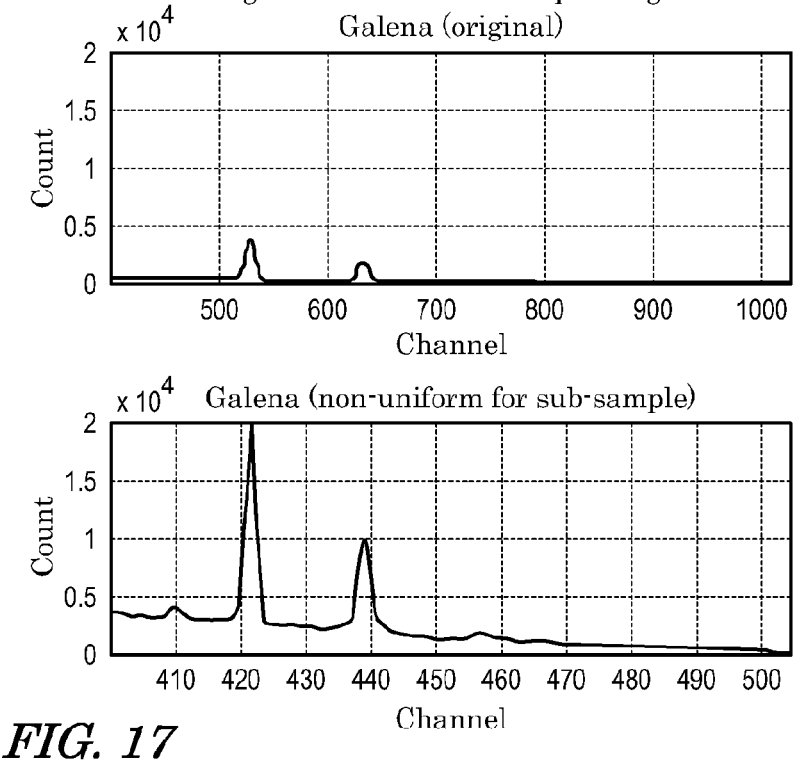
FIG. 17 shows magnified view of sub-sampled region.

2. For the remaining data (i.e. above 8 keV), accumulate six consecutive channels to form a new channel. This has the effect of increasing the height of all data within this region, and will reinforce peaks while leaving the noise spread out. FIG. 16 shows the original Galena (lead-sulphide) mineral before and after this processing. In standard operating conditions of the described system, the processing changes the number of channels in a spectrum from 1024 to 504. FIG. 17 shows the channels for 8 keV-25 keV for the original and sub-sampled spectra. The original Galena mineral peak at channel 527 is approximately 3000 photons, compared to 45,000 photons for the peak at channel 117. After processing, this peak has increased in height to 20,000 photons (approximately a factor of 6), while decreasing the number of channels in this region by a factor of 6. This assists in the discrimination between similar elements because the small peaks suddenly become far more important in the least squares fitting. It also reduces the processing time significantly because fewer channels are processed.

Low Count Channel Optimization

Figure 18:
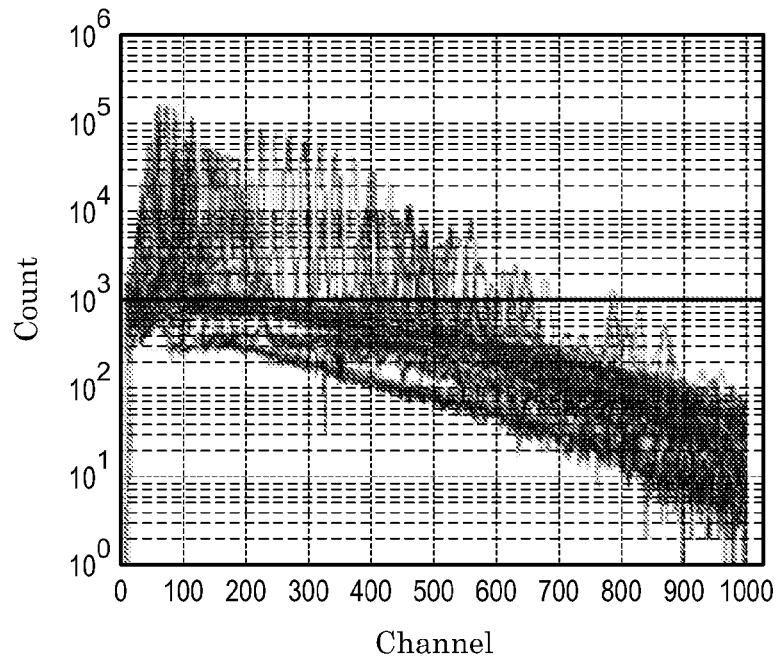
FIGS. 18 and 19 show template spectra obtained without and with non-uniform sub-sampling, respectively.
Figure 19:
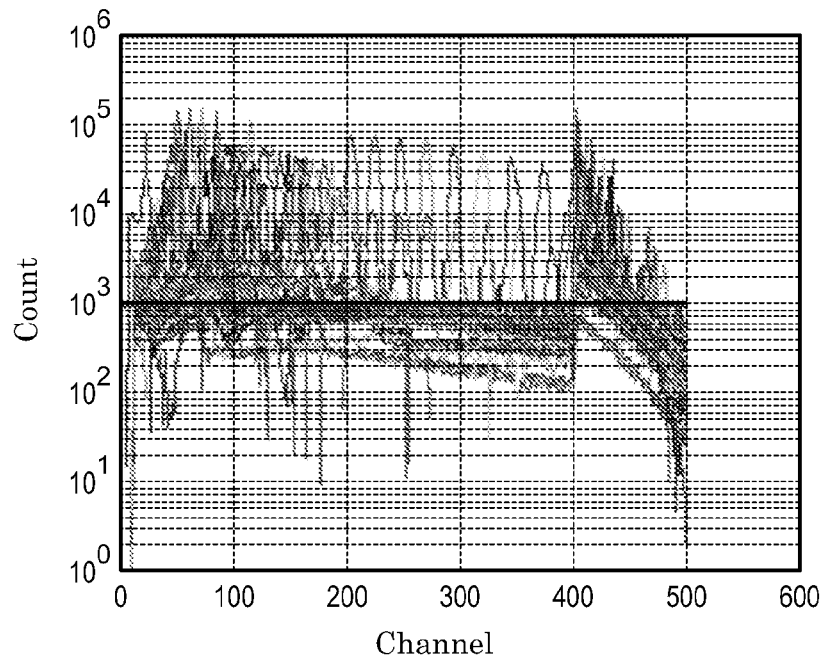

The algorithm optimizes the analysis by reducing the number of channels analyzed for the spectrum based on the templates used and the number of photons in the spectrum. For example, low count spectra generally have no peaks at higher energies because there aren't enough photons detected at those energies to create a statistically meaningful peak. FIG. 18 shows an overlay of 45 million count spectra for the elemental templates. If a random spectrum is analyzed which contains only 1000 counts, then any peaks below the thick horizontal line are unlikely to be created because the probability that a photon will be detected there is less than 1/1000. Therefore, it isn't necessary to analyze all 1024 channels for a 1000 count analysis, and thus the number of channels analyzed can be reduced to about 800. This range is dynamically generated based on the templates used for analysis, and increases the computation speed for each iteration. The low count channel optimization is performed after the non-uniform sub-sampling. This reduces the upper channel from about 800 to about 480 for a 1000 count analysis, as shown in FIG. 19.

Calculate Iterative Least Square Solution

Iterative Least Squares Initialization

Figure 20:
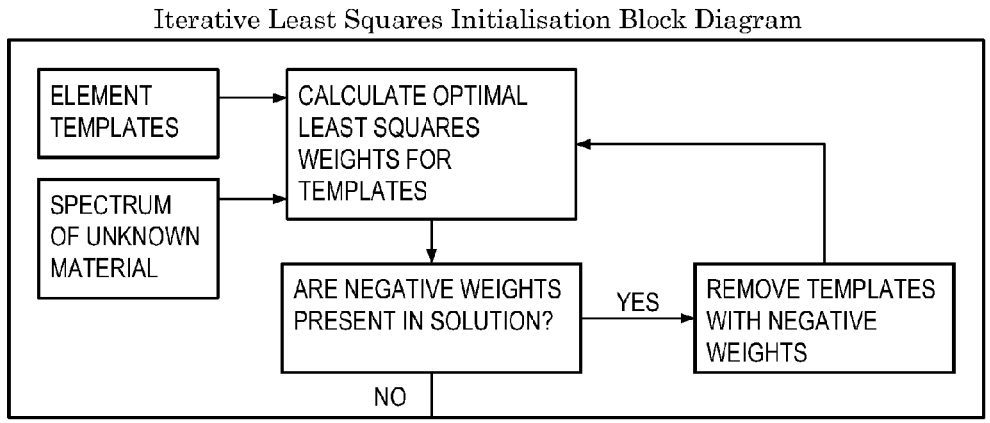
FIG. 20 shows interative least squares initialization block diagram.

FIG. 20 shows the block diagram for a proposed algorithm for iterative least squares initialization. The purpose is to quickly remove artefact elements from the solution by purging elements whose concentration is negative. When the elemental concentration is calculated, there are no restrictions on the weights calculated for each element. Thus, this algorithm uses the fact that elements can't have negative concentration as the rule to remove elements. Once there are no negative concentration elements then the stage has completed. The calculation to generate the optimal weights uses the standard linear least squares algorithm. The least squares algorithm solves an over-determined system of linear equations of the form $$Ax=b \qquad \text{(Equation 1: Linear equation to be solved)}$$

where:

A is the matrix of known data points;

b is final solution; and x is the set of unknowns which linearly scale the known matrix A to generate the vector b.

In the presently disclosed approach, A represents the known element templates, b represents the spectrum being analyzed, and x is the multiplication factor applied to each template to generate the spectrum. This is solved as follows $$X=(A^TA)^{-1}A^Tb \qquad \text{(Equation 2: Least squares solution)}$$

This calculates the optimal set of weights that minimize the squared error $$e=\|Ax-b\|^2 \qquad \text{(Equation 3: Error term minimized by Equation 2)}$$

Figure 21:
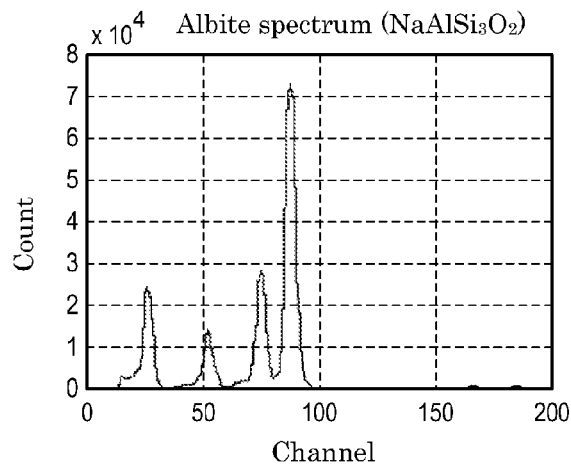
FIG. 21 shows albite spectrum ($NaAlSi_3O_2$).

In FIG. 21 the spectrum of the mineral albite is shown. The four peaks are generated by the elements oxygen, sodium, aluminium and silicon respectively. The "concentration" of each element is calculated to minimize the squared error, not to calculate the composition of the mineral. Thus, they are not concentrations but actually represent a multiplier with respect to the reference spectrum for each element. These multipliers are not guaranteed to lie between 0 and 100% but could be any value. In addition, some elements may have negative concentrations, because they are creating "anti-peaks" which are in turn used to offset artefact peaks of other elements that aren't present. This effect is demonstrated in FIG. 22, FIG. 23 and FIG. 24.

Figure 22:
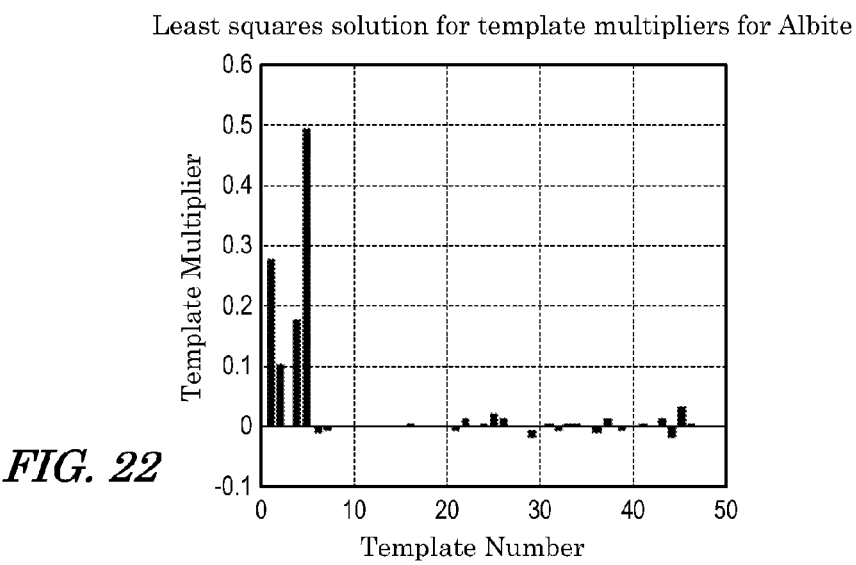
FIG. 22 shows raw template multipliers for albite after $1^{st}$ iteration.
Figure 23:
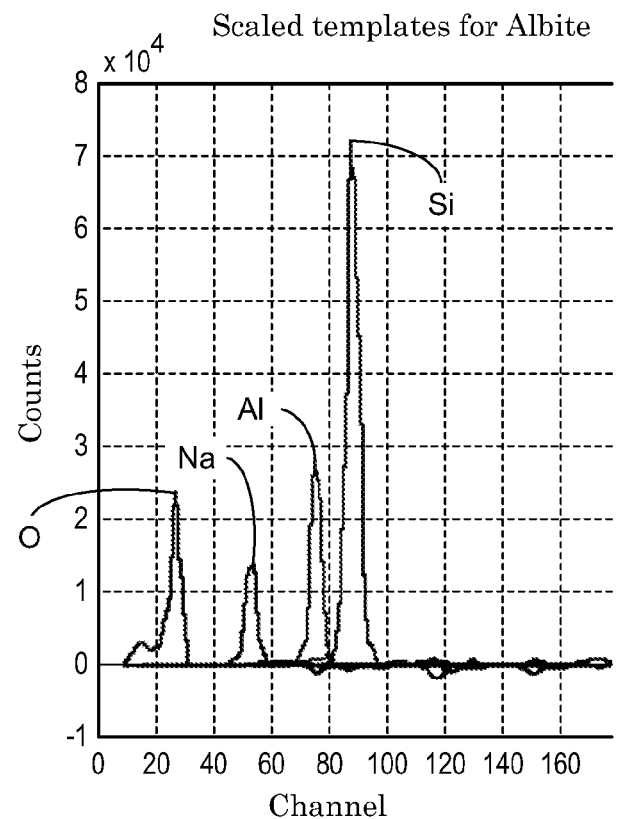
FIG. 23 shows scaled templates for albite.
Figure 24:
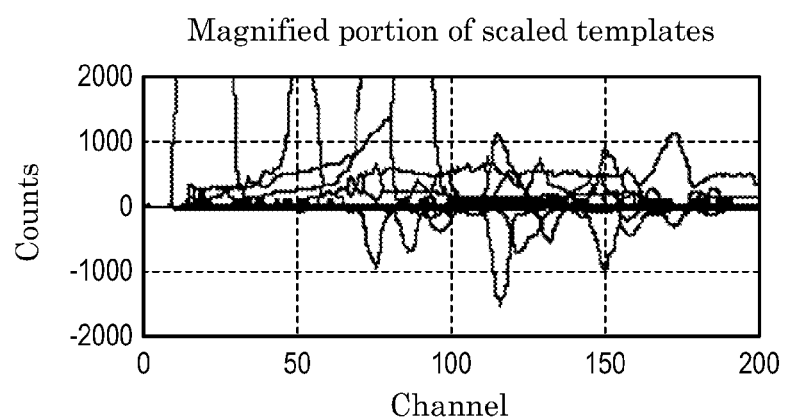
FIG. 24 shows magnified portion of scaled templates.

FIG. 23 shows each of the element templates after they've been scaled by the values shown in FIG. 22. The four main elements, oxygen, sodium, aluminium and silicon, stand out quite strongly for this mineral. FIG. 24 shows that some of the peaks introduced into the solution are being cancelled out by the presence of anti-peaks. If the elements which generate the anti-peaks are removed, the template multipliers for the remaining elements can be improved. In order to reduce the artefact elements, all elements with concentrations below 0.0 are removed and the solution is re-calculated. This process is repeated until there are no more negative concentrations. This removes most of the artefact elements from the mineral. The entire process can be summarised as follows:

1. Generate the matrix A from the set of templates (accounting for template spectra live time)
2. Solve for the optimal weights for x
3. If any negative concentrations are present in x, remove those corresponding templates from A, or equivalently, set the weight corresponding to those elements to zero, and go back to step 1.

Substitute Background Elements

Figure 25:
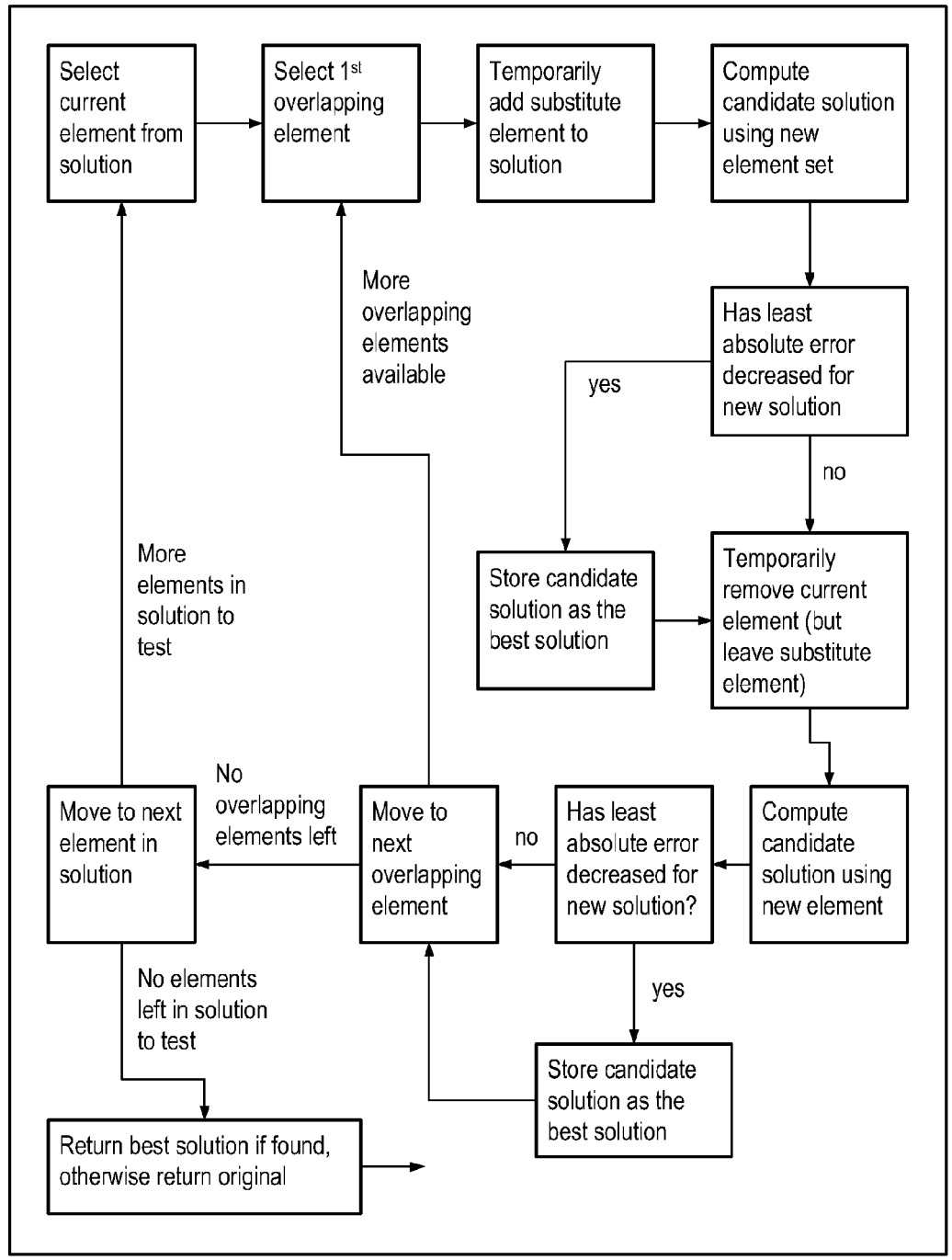
FIG. 25 shows background element substitution algorithm.

This phase of the processing analyzes the solution and substitutes a pre-defined set of overlapping elements for each element in the solution. The purpose of this phase is to determine whether an element has been removed from the solution prematurely and to restore it if so. The algorithm outline is shown in FIG. 25.

This phase scans through each element and verifies whether any of the elements is listed with overlapping elements. If so, each overlapping element is added to the composition, one at a time, and the composition is re-computed. The algorithm also tries substituting each of the overlapping elements for the original element. It tests whether the composition has improved by examining the absolute error of the synthesised spectrum given by the composition against the original. A list of overlapping elements is shown in Table 1.

TABLE 1

| Reference Element | Overlapping element 1 | Overlapping element 2 | Overlapping element 3 | Overlapping element 4 |
|---|---|---|---|---|
| Fluoride | Manganese | Iron | | |
| Sodium | Zinc | | | |
| Aluminium | Bromine | | | |
| Silicon | Strontium | Tungsten | Tantalum | Rubidium |
| Phosphorous | Zirconium | Platinum | Iridium | Yttrium |
| Sulfur | Molybdenum | Iron | | |
| Chlorine | Sodium | Rubidium | | |
| Potassium | Indium | | | |
| Calcium | Antimony | | | |
| Vanadium | Oxygen | | | |
| Chromium | Vanadium | Manganese | | |
| Manganese | Flourine | Europium | | |
| Iron | Manganese | Cobalt | Fluorine | |
| Cobalt | Iron | Nickel | | |
| Nickel | Cobalt | | | |
| Zinc | Sodium | | | |
| Bromine | Aluminium | | | |
| Redium | Silicon | Tungsten | Titanium | |
| Strontium | Silicon | Tungsten | | |
| Yttrium | Osmium | Phosphorous | | |
| Zirconium | Platinum | Phosphorous | Indium | |
| Niobium | Mercury | | | |
| Molybdenum | Sulfur | Gold | | |
| Ruthenium | Chlorine | | | |
| Rhedium | Chlorine | | | |
| Silver | Thorium | | | |
| Cadmium | Uranium | | | |
| Indium | Potassium | | | |
| Antimony | Calcium | | | |
| Bromine | Titanium | | | |
| Praseodymium | Lanthanum | | | |
| Neodymium | Carbon | | | |
| Europium | Manganese | | | |
| Terbium | Iron | | | |
| Dysprosium | Iron | | | |
| Tantalum | Silicon | Tungsten | Rubidium | Copper |

TABLE 1-continued

| Reference Element | Overlapping element 1 | Overlapping element 2 | Overlapping element 3 | Overlapping element 4 |
|---|---|---|---|---|
| Tungsten | Silicon | Strontium | Tungsten | Rubidium |
| Osmium | Yttrium | | | |
| Indium | Zirconium | Platinum | Phosphorous | |
| Platinum | Zirconium | Phosphorous | Indium | |
| Mercury | Niobium | | | |
| Gold | Sulfur | Molybdenum | | |
| Thorium | Sulfur | | | |
| Uranium | Cadmium | | | |

Purge Oxygen Below 5%

This is an optional single processing step which can be implemented either at this stage of the algorithm, or in the stage of purging trace elements, described later in the text. In particular, this step removes oxygen if the concentration is below 5%. This arbitrary threshold was reached after analysing all 76 minerals and elements and determining that this threshold was appropriate to retain oxygen that was indeed present in the minerals. At the same time the chosen concentration also allowed to successfully remove from the calculations oxygen that was merely an artefact. This reduces the amount of trace oxygen reported for all results. The purpose of this stage is to reduce the complexity of the results reported.

Iterative Absolute Error Refinement

Figure 26:
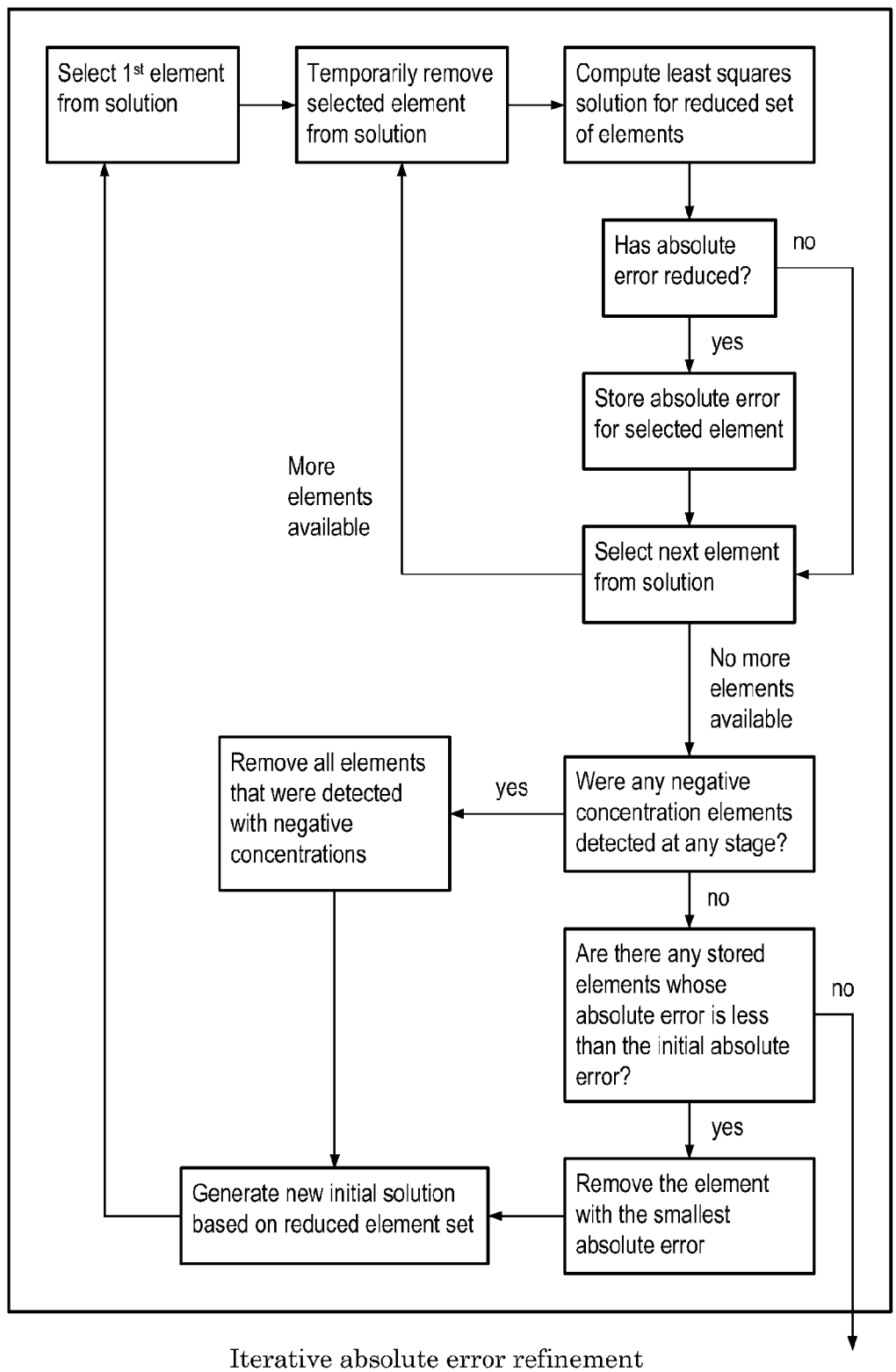
FIG. 26 shows interative absolute error refinement.

FIG. 26 shows the block diagram for the iterative absolute error refinement stage. The purpose of this stage is to remove element artefacts from the composition by minimising the absolute error between the synthesised spectrum and the source spectrum. It iterates through the elements and removes each element one at a time. It then recomputes the concentrations of the remaining elements and checks if the absolute error has decreased. This is repeated for all elements. It then removes the element that had the largest decrease in error, and repeats the process iteratively.

Element Overlap Resolution

Figure 27:
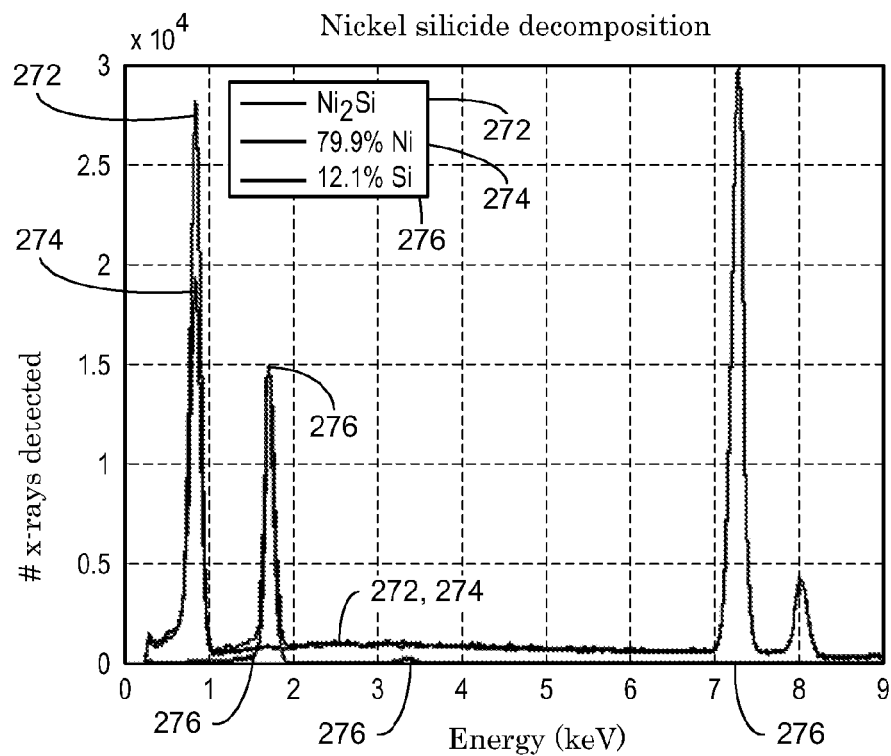
FIG. 27 shows simple two element spectral analysis of nickel silicide.

This is a final processing stage which represents a set of rules for removing certain elements if their overlapping element (see Table 2) is also present. The stage is designed to remove elements that may appear to be in the spectrum, but are usually the result of matrix effects distorting the mineral spectrum and altering the relative intensity of element peaks. For example, the synthetic mineral nickel silicide ($Ni_2Si$) consists of nickel (plot 274) and silicon (plot 276). If the relative heights of the nickel K and L peaks are compared for $Ni_2Si$ and pure nickel, the $Ni_2Si$ Lα peak 272 (851 eV) is significantly taller than expected, as shown in FIG. 27.

The increase in height is caused by x-rays generated from the silicon interacting with the nickel atoms and generating additional x-rays. This causes the spectral fitting to match poorly for this peak, and other elements may be added to the solution to try to reduce the mismatch. This stage is designed to detect elements that may have been added incorrectly and to remove them.

During this stage, the solution for pairs of elements is analyzed and, if both elements are found, one of the elements is removed. The relative concentration of each element pair is stored, because some of the elements can occur in minerals together (such as molybdenum and sulphur), but others do not (such as thorium and silver). In the case where they do not occur together, the relative concentration required is 0, which means that the less common element will always be removed if both have been reported in the composition. The higher the relative concentration required, the more difficult it is to remove the potentially overlapping elements. The relative concentrations specified here have been derived empirically from a test set, and may not represent the optimal set of relative concentration thresholds for all minerals.

TABLE 2

Table 5-2: Heuristic Elemental Removal Rules

| Elements Present | Element Removed | Relative concentration required |
|---|---|---|
| Sodium, zinc | Sodium | 2 |
| Phosphorous, Yttrium | Phosphorous | 4 |
| Phosphorous, Zirconium | Phosphorous | 3 |
| Gallium, Sodium | Gallium | 0 |
| Aluminum, Bromine | Bromine | 0 |
| Strontium, Silicon | Strontium | 5 |
| Zirconium, Platinum | Zirconium | 5 |
| Molybdenum, Sulfur | Molybdenum | 0 |
| Indium, Potassium | Indium | 0 |
| Cerium, Venadium | Cerium | 0.5 |
| Cerium, Chromium | Cerium | 2.7 |
| Neodymium, Chromium | Neodymium | 1 |
| Europium, Manganese | Europium | 0.5 |
| Europium, Iron | Europium | 0.5 |
| Terbium, Iron | Terbium | 0.5 |
| Dysprosium, Iron | Dysprosium | 5 |
| Holmium, Iron | Holmium | 3 |
| Holmium, Cobalt | Holmium | 0.5 |
| Erbium, Iron | Erbium | 0 |
| Thulium, Copper | Thulium | 0.5 |
| Thulium, Aluminium | Thulium | 5 |
| Thulium, Iron | Thulium | 10 |
| Ytterbium, Nickel | Ytterbium | 5 |
| Ytterbium, Zinc | Ytterbium | 4 |
| Hafnium, Nickel | Hafnium | 6 |
| Tantalum, Silicon | Tantalum | 1 |
| Tantalum, Zinc | Tantalum | 0 |
| Tantalum, Copper | Tantalum | 3 |
| Tungsten, Silicon | Tungsten | 3.5 |
| Rhenium, Zinc | Rhenium | 7.0 |
| Osmium, Zirconium | Osmium | 10.0 |
| Thorium, Silver | Thorium | 2.0 |

Purge Trace Elements

This step removes trace elements from the solution and normalises the result. It uses a magic threshold of less than 2.5% as the criteria for retaining elements. The reason is that elements of such a low concentration are generally artefacts in the composition rather than being present. The specific threshold for elements being removed in the currently disclosed system and method is approximately 0.5%. The solution is then normalized to 100%.

Calculate Element Peak Ratios

This stage is required because the element ratios up to this point refer to the optimal set of multiplication factors required to fit the element spectra to the unknown mineral. However, the final output of the spectrum processing must be a weight percentage per element, which requires a matrix correction. The ZAF corrections applied at the end require that the elements are quantified relative to a single peak rather than for the entire spectrum. Therefore, this stage computes the peak ratio of each element and specifies the peak that was used to calculate the percentage.

Figure 28:
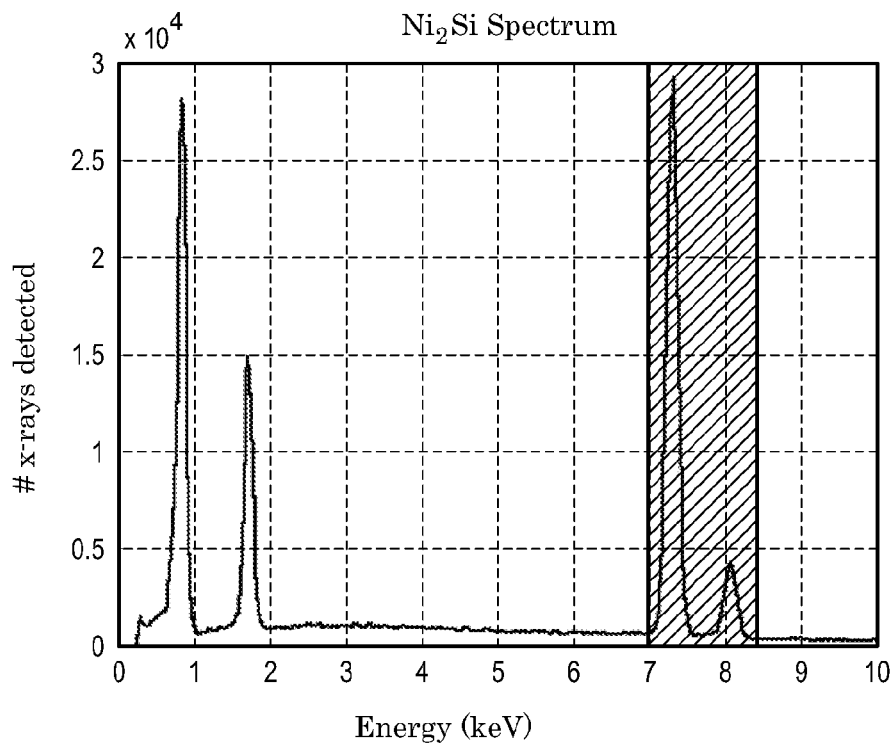
FIG. 28 shows $Ni_2Si$ spectrum.

The peak for each element is determined, and the ratio for that peak is computed. It is desirable to use higher energy peaks because they are not subject to as many ZAF effects as lower energy peaks. In the presently described method, the highest peak for each element is selected for which the ratio of the beam energy to the peak energy does not exceed 2.5. Therefore, when using a beam voltage of 25 kV, the selected highest peak has voltage of 10 kV or less. In the case of nickel (in $Ni_2Si$), this is the K peak at 7477 eV (FIG. 28).

However, when overlapping elements are present, the peak ratios cannot be calculated individually because emissions from the other elements are often contributing significantly to a particular peak. FIG. 29 shows a portion of the spectrum for the mineral "monazite" (plot 292) which contains several rare earth elements, such as La (plot 294), Ce (plot 296), Pr (plot 297), Nd (plot 298) and Th (plot 299). The spectra 297 for Pr and the spectrum 298 for Nd have been highlighted to illustrate that these cannot be computed in isolation of the other elements because there are significant overlapping portions of the spectra from other elements.

Fortunately, the existing technique of computing the element concentration can be directly applied to computing the peak ratios by using Equation 2. However, rather than compute the solution for the entire spectrum, the technique uses as much of the spectrum as possible, and removes the other peaks. FIG. 30 shows a diagrammatic representation of this computation for computing the nickel K peak ratio. The nickel L peak is omitted from the calculation, but otherwise it directly solves for the peak ratio by solving equation 2.

Figure 31:
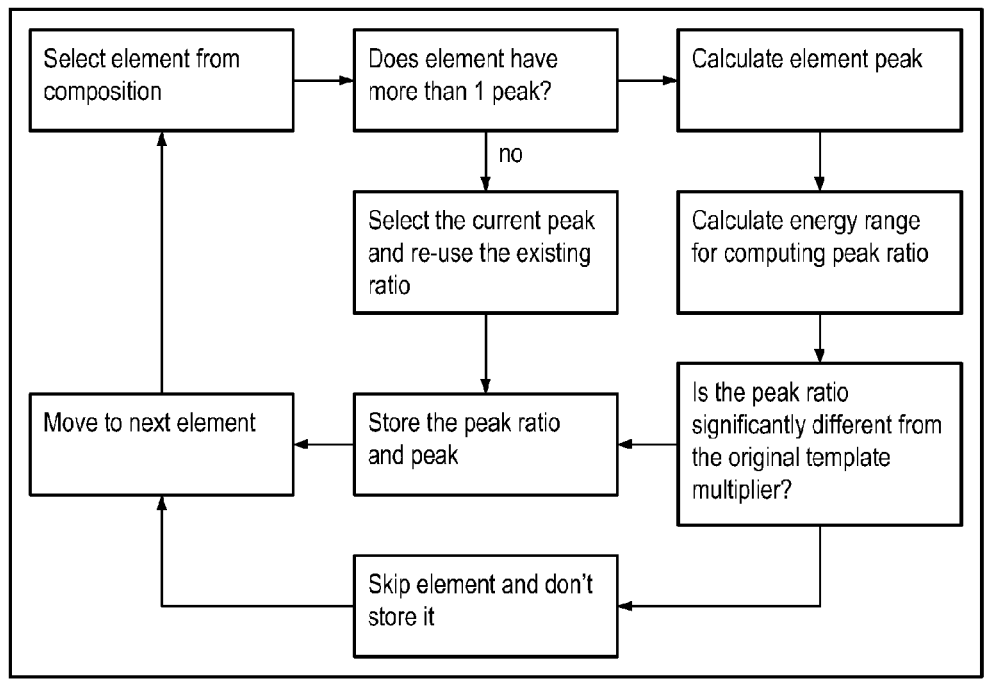
FIG. 31 shows peak ratio calculation block diagram.

A block diagram for this computational algorithm is shown in FIG. 31. The algorithm attempts to prevent having to compute the peak ratios for elements that only have one peak (such as magnesium) by reusing the existing result. All elements below Argon (Z=18) have one peak. In addition, in the standard operating conditions of the presently disclosed method, the beam voltage is 25 keV. Consequently, the elements Pd, Ag, Cd, In, Sn, Sb, Te and I only have one peak, because the K peak is higher than the beam voltage and they do not have any M peaks. This provides a minor performance optimization by avoiding recomputing the peak ratios for these elements.

The algorithm also contains a second path which drops elements from the composition if their concentration changes significantly. This is intended to catch elements that have been reported in trace amounts, but whose concentration increases by a factor of 10×, if a single peak is analyzed in isolation.

ZAF Corrections

The peak ratios are corrected using ZAF corrections prior to being reported.

Processing Time

Figure 32:
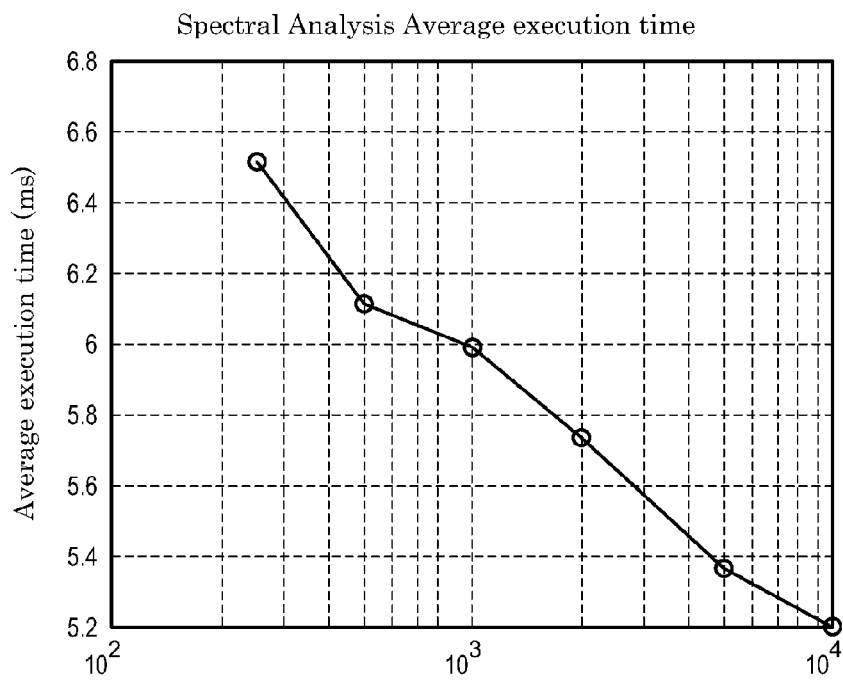
FIG. 32 shows average processing time.
Figure 33:
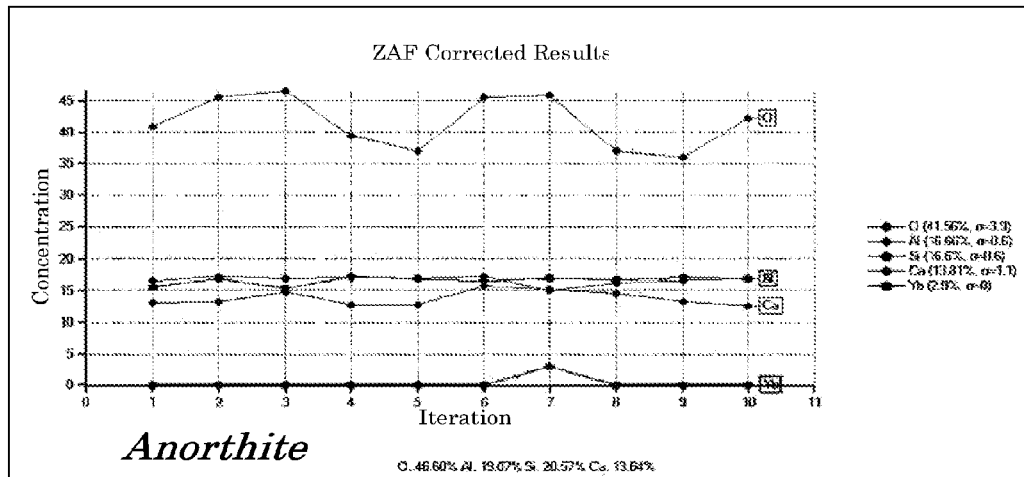
FIGS. 33 to 48 show the compositions of various minerals calculated by way of the algorithm of the present invention.
Figure 34:
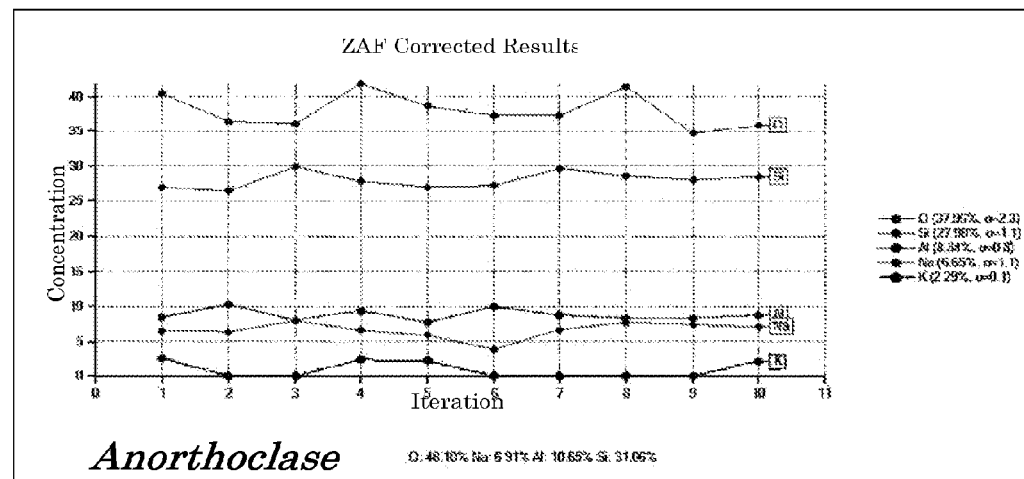
Figure 35:
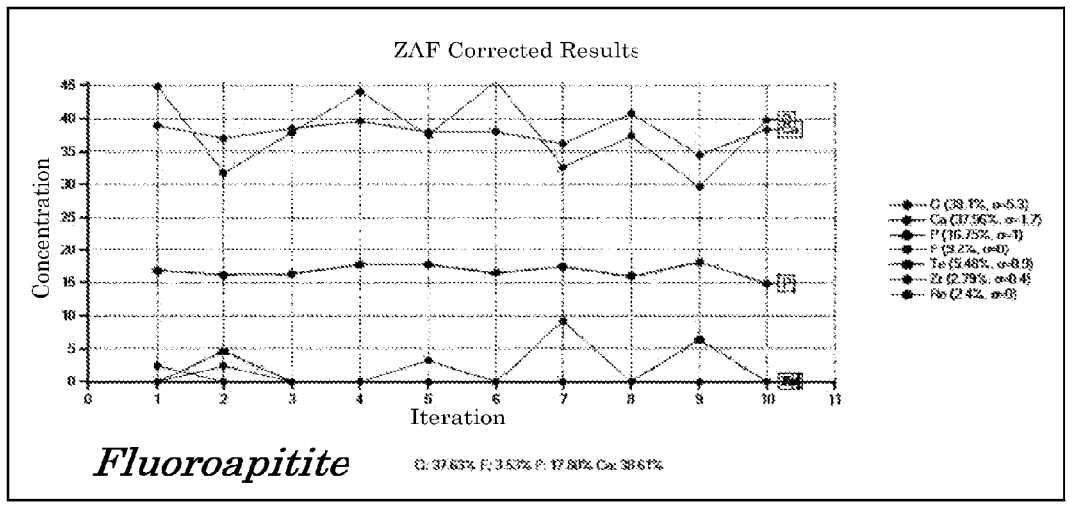
Figure 36:
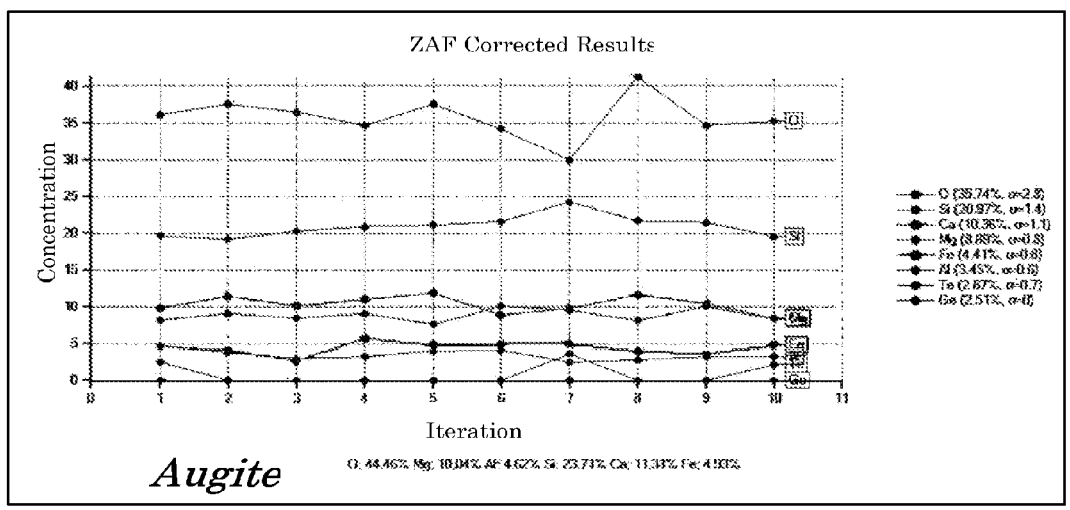
Figure 37:
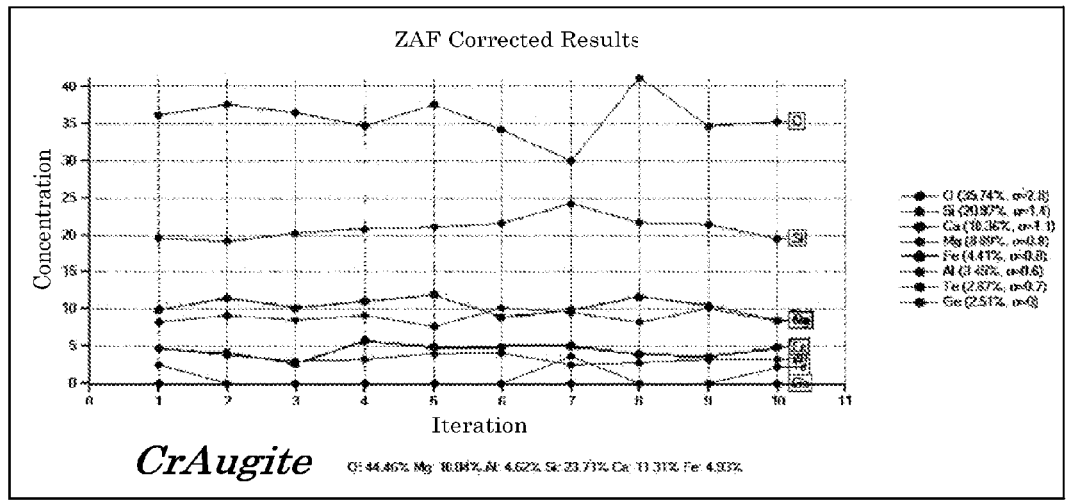
Figure 38:
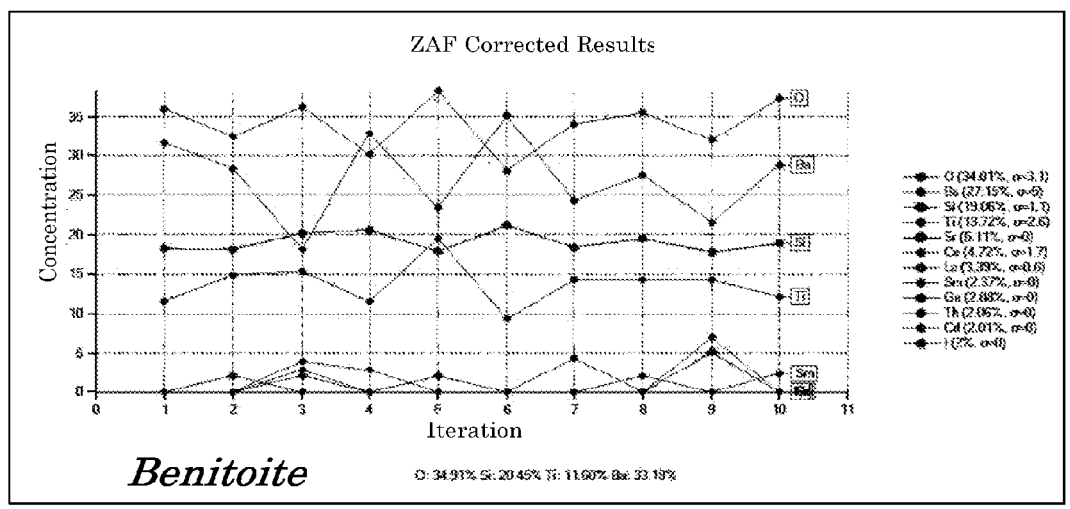
Figure 39:
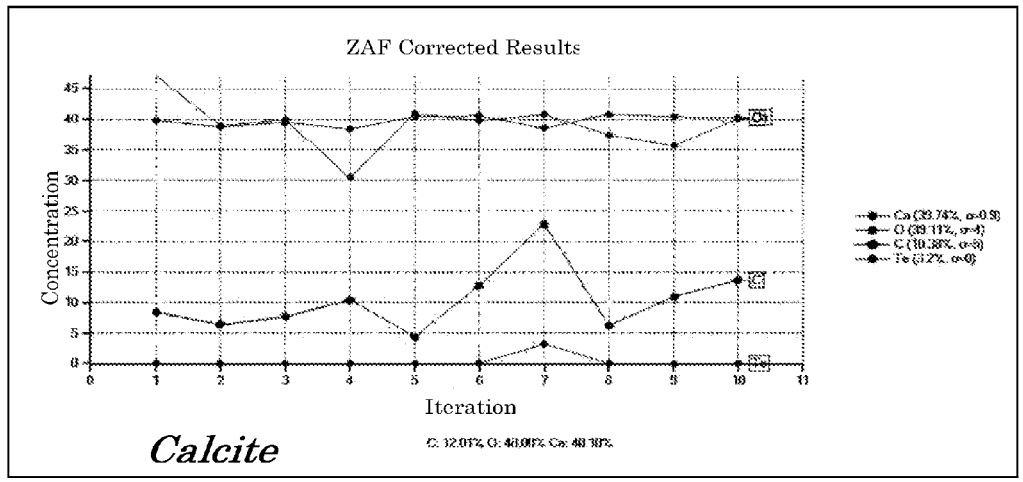
Figure 40:
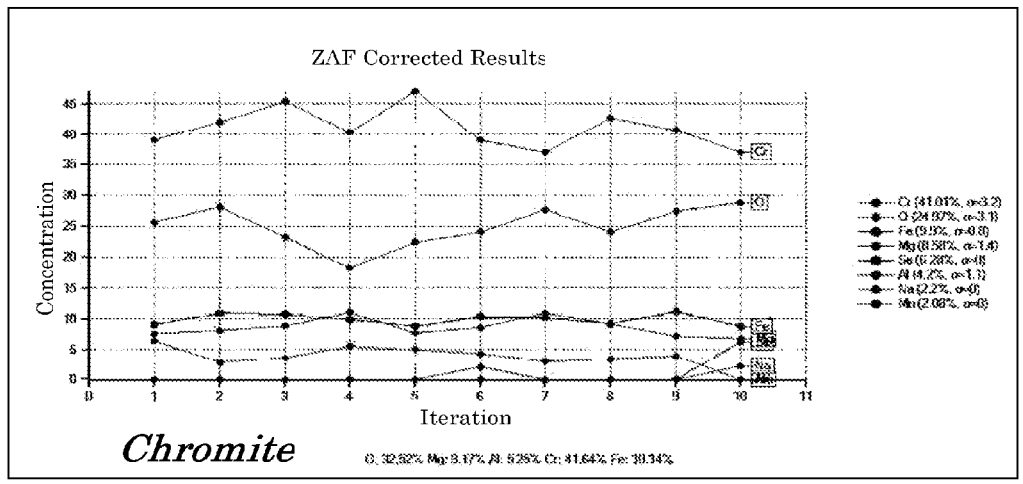
Figure 41:
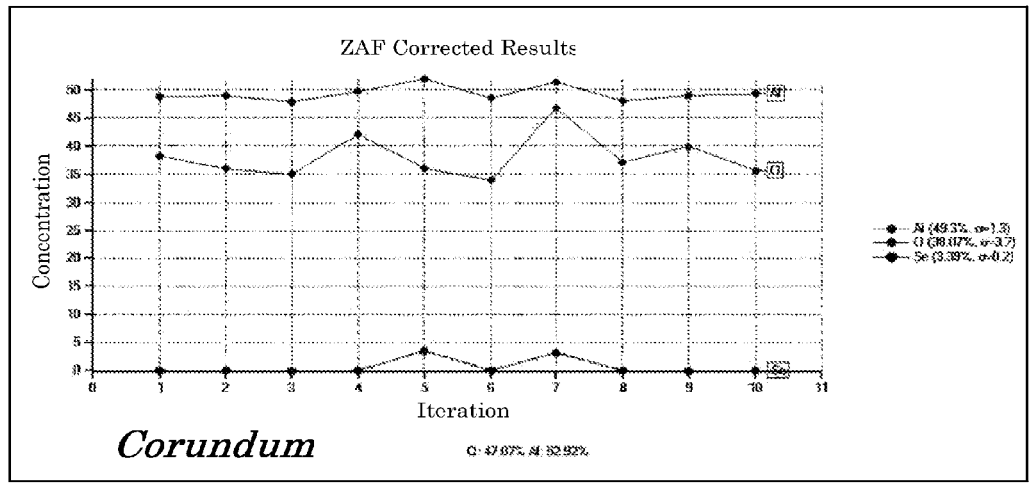
Figure 42:
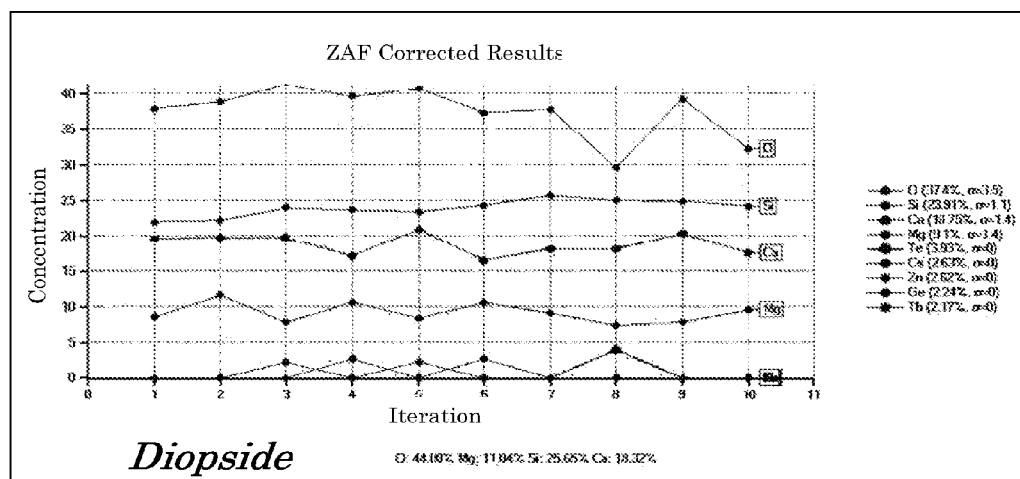
Figure 43:
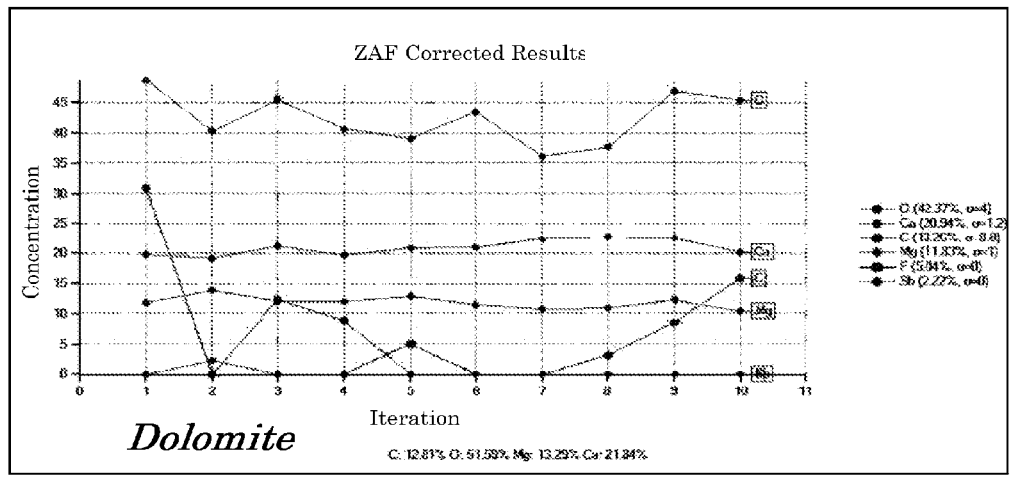
Figure 44:
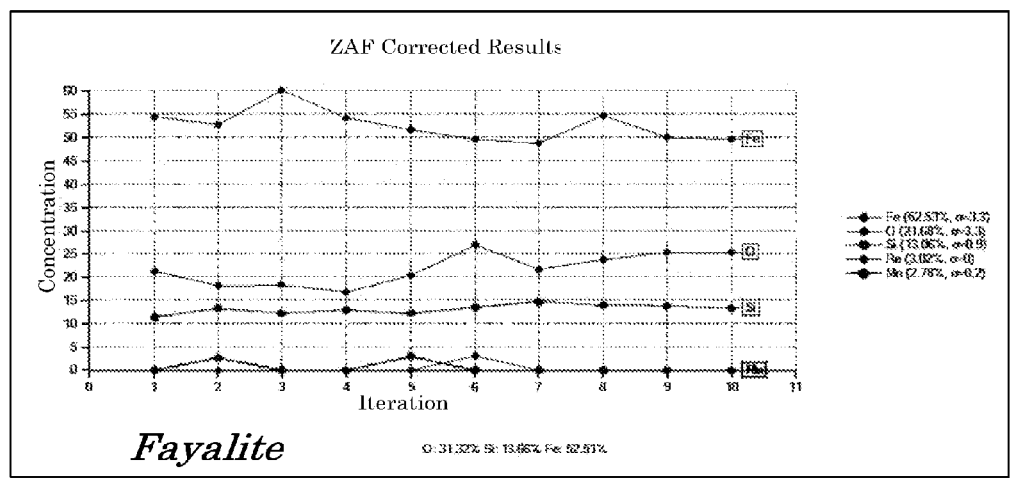
Figure 45:
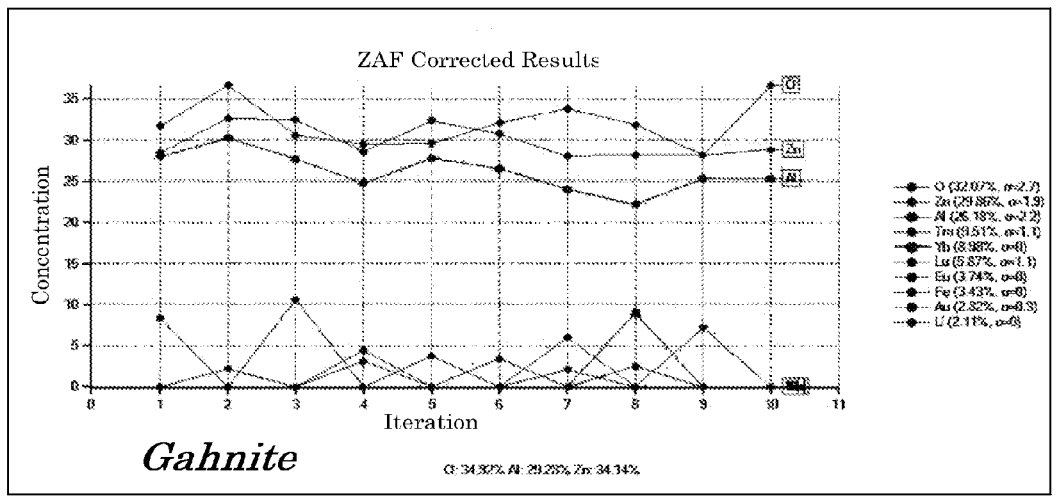
Figure 46:
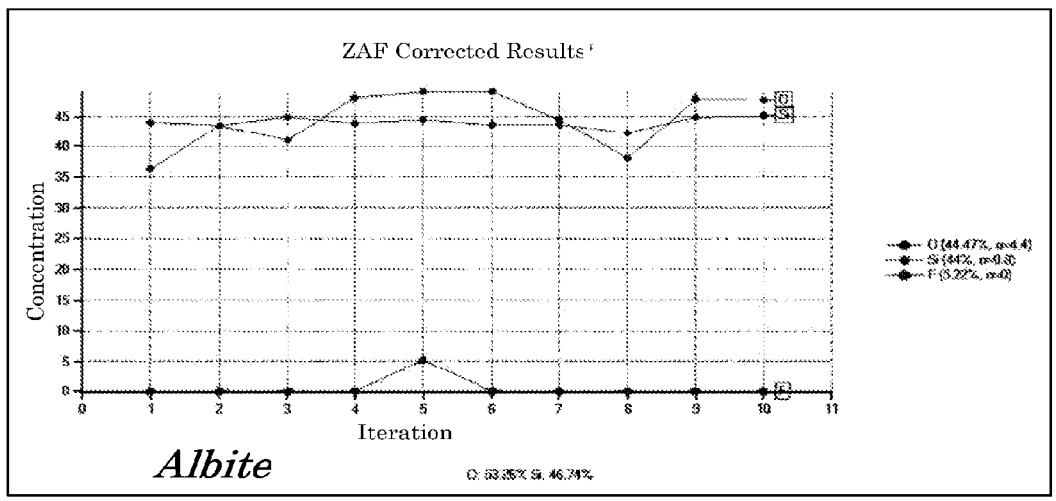
Figure 47:
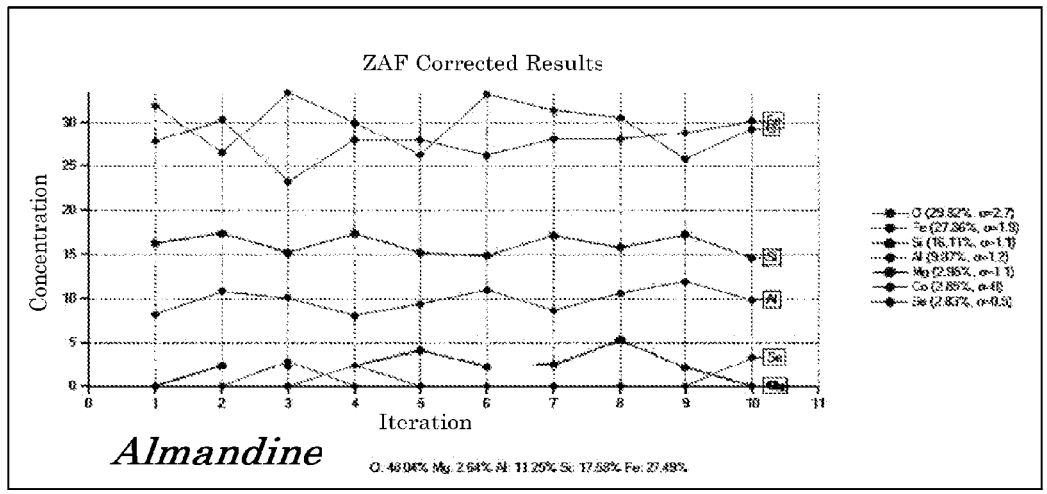
Figure 48:
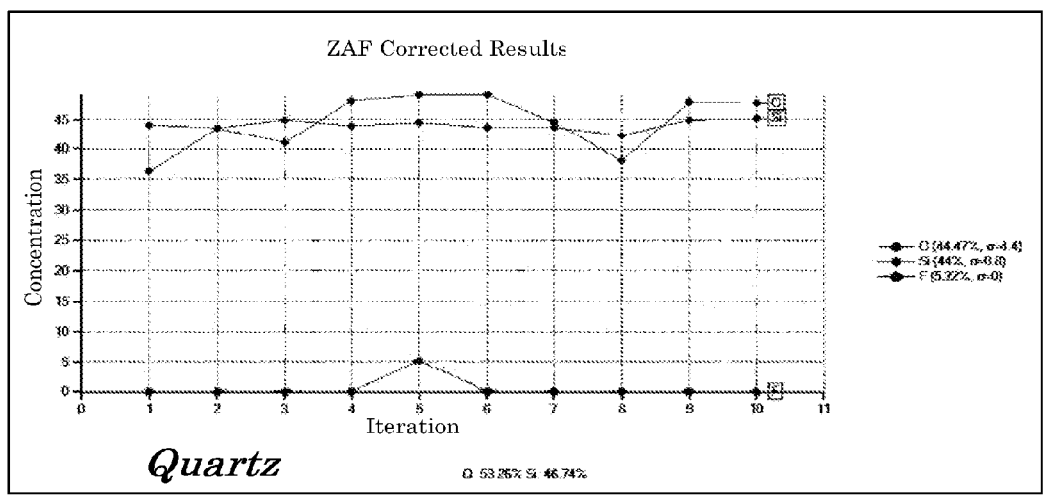

The processing time for the algorithm was targeted at 10 milliseconds for a 1000 count spectrum. FIG. 32 shows the average execution time of the entire spectral analysis engine when analysing the set of minerals from the SPI_MINERALS and Smithsonian standard blocks. The processing time was found to be inversely proportional to the number of counts in the spectrum. This is expected, because the spectrum becomes smoother at higher counts and it is less difficult to establish the correct set of elements, and there are fewer incorrect elements that need refining or exchange.

The longer than expected processing time may be associated with some programming overhead translating between the managed C# code and the unmanaged C++ spectral analysis engine code. The execution time is also proportional to the number of elements used for analysis. The figures shown in FIG. 32 were generated when analysing with 72 elements.

Whereas convention x-ray spectroscopy analysis uses millions of counts that are accumulated on the order or a second or more, to produce a sufficiently smooth curve for conventional analysis, embodiments of the present invention can use fewer than 100,000 counts, fewer than 50,000 counts, fewer than 10,000 counts, fewer than 3000 counts, fewer than 1000 counts or fewer than 500 counts, depending on the accuracy required. Using a typical silicon drifted x-ray detector in which having a surface area of between 10 mm$^2$ and 30 mm$^2$ and subtending a solid angle of about 0.3 sr, embodiments of the present invention can determine the elements present in a sample in less than one hundred milliseconds, less than a ten milliseconds, and in some embodiments, on the order of a few milliseconds.

Results

Some composition results of the described method for spectral analysis are shown in FIGS. 33 to 47. The theoretical composition of each mineral is listed at the bottom of each plot. The mean and standard deviation of each result is reported in the legend of each plot. Each of these analyzes was performed at 1000 counts. The main observations that can be made is that carbon and oxygen vary far more widely than other elements. Secondly, low concentration elements may appear or disappear from the composition if their composition is too small. Finally, artefact elements are present in nearly every composition, but at low concentrations.

Hardware Embodiment

Figure 49:
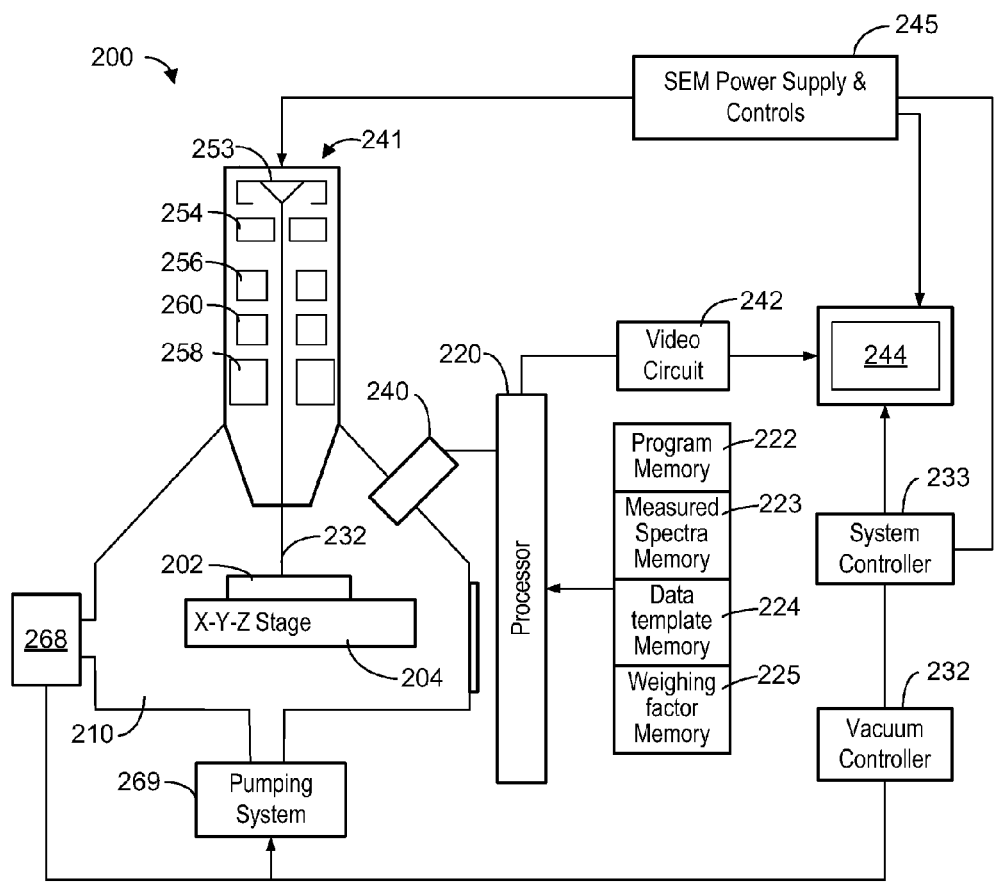
FIG. 49 shows a typical electron beam system embodying the present invention.

FIG. 49 shows a scanning electron beam system 200 with an x-ray detector 240 suitable for practicing embodiments of the present invention. A scanning electron microscope 241, along with power supply and control unit 245, is provided with system 200. An electron beam 232 is emitted from a cathode 253 by applying voltage between cathode 253 and an anode 254. Electron beam 232 is focused to a fine spot by means of a condensing lens 256 and an objective lens 258. Electron beam 232 is scanned two-dimensionally on the specimen by means of a deflection coil 260. Operation of condensing lens 256, objective lens 258, and deflection coil 260 is controlled by power supply and control unit 245.

A system controller 233 controls the operations of the various parts of scanning electron beam system 200. The vacuum chamber 210 is evacuated with ion pump 268 and mechanical pumping system 269 under the control of vacuum controller 232.

Electron beam 232 can be focused onto sample 202, which is on movable X-Y stage 204 within lower vacuum chamber 210. When the electrons in the electron beam strike sample 202, the sample gives off x-rays whose energy correlated to the elements in the sample. X-rays 232 having energy inherent to the elemental composition of the sample are produced in the vicinity of the electron beam incident region. Emitted x-rays are collected by x-ray detector 240, preferably an energy dispersive detector of the silicon drift detector type, although other types of detectors could be employed, which generates a signal having an amplitude proportional to the energy of the detected x-ray.

Output from detector 240 is amplified and sorted by the processor 220, which counts and sorts the total number of X-rays detected during a specified period of time, at a selected energy and energy resolution, and a channel width (energy range) of preferably between 10-20 eV per channel. Processor 220 can comprise a computer processor; operator interface means (such as a keyboard or computer mouse); program memory 222 for storing data and executable instructions; interface means for data input and output, executable software instructions embodied in executable computer program code; and display 244 for displaying the results of a multivariate spectral analysis by way of video circuit 242.

Processor 220 can be a part of a standard laboratory personal computer, and is typically coupled to at least some form of computer-readable media. Computer-readable media, which include both volatile and nonvolatile media, removable and non-removable media, may be any available medium that can be accessed by processor 220. By way of example and not limitation, computer-readable media comprise computer storage media and communication media. Computer storage media include volatile and nonvolatile, removable and non-removable media implemented in any method or technology for storage of information such as computer-readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by processor 220.

Program memory 222 can include computer storage media in the form of removable and/or non-removable, volatile and/or nonvolatile memory and can provide storage of computer-readable instructions, data structures, program modules and other data. Generally, the processor 220 is programmed by means of instructions stored at different times in the various computer-readable storage media of the computer. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described below in conjunction with a microprocessor or other data processor. The invention also includes the computer itself when programmed according to the methods and techniques described herein.

An x-ray spectrum obtained as described above can be stored in a portion of memory 222, such as the measured spectra memory portion 223. Data template memory portion 224 stores data templates, such as known spectra of elements or, in some embodiments, known diffraction patterns of materials. Weighing Factor Memory portion 225 stores weighting factor for each of the data templates, the weighting factors combining with the data templates to produce a calculated spectrum approximating the measured spectrum. The weighting factors correlated to the abundance in the sample of the element corresponding to the data template. Processor 220 uses the methods described above to minimize an error value which represents the different between the measured pattern and the combination of the data templates and weighting factors.

While the embodiment shown includes a scanning electron microscope, related embodiment could use a transmission electron microscope or a scanning transmission electron microscope to generate x-rays from the sample. An x-ray fluorescence system could also be used to generate x-rays from the sample. Other embodiments may detect other characteristic radiation, such as gamma rays, from a sample.

CONCLUSIONS

The compositions reported are affected by a number of factors outside of the algorithm of this engine. The definition of the standards used as pure elements was not defined. Although some elements standards, such as gold or iron can be measured directly, other elements must be derived from minerals because they cannot be measured directly. For example, oxygen is derived by measuring quartz ($SiO_2$) and silicon, and subtracting a portion of the silicon from the quartz spectrum. This is repeated for a large number of elements to create the full element list. Therefore, these derived elements may not be as accurate in their spectra or lifetime.

Consequently, additional work is underway to improve the quality of the standards, irrespective of the algorithm presented here.

As used herein, the term spectrum includes any property that is represented by an intensity graph including for example, an x-ray or a diffraction pattern.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method of spectrum data analysis, the method comprising the steps of:
   directing an electron beam toward an unknown material;
   collecting x-rays emitted from the unknown material as a result of the electron beam impact;
   determining from the energies of less than 100,000 collected x-rays a spectrum of the unknown material;
   providing a set of element data templates, each corresponding to an x-ray spectra of a chemical element;
   calculate least squares weights for the element data templates in approximating the spectrum;
   removing one or more of the templates having negative weights in approximating the spectrum; and
   re-calculating an approximation of the spectrum with said one or more templates removed.

2. The method as claimed in claim 1, further comprising the steps of:
   after re-calculating the approximation of the spectrum with said one or more templates removed,
   selecting one element of the approximation;
   replacing said one element with an overlapping element;
   calculating a candidate solution with the template of the overlapping element instead of the template of said one element;
   determining whether a least absolute error has decreased for the candidate solution; and
   storing the candidate solution as an updated approximation of the spectrum if the least absolute error has decreased.

3. The method as claimed in claim 2, wherein said one element is iteratively replaced with two or more overlapping elements.

4. The method as claimed in claim 1, wherein the method further comprises the steps of:
   after re-calculating the approximation of the spectrum with said one or more templates removed,
   selecting one element of the approximation;
   calculating a least squares candidate solution for a reduced set of elements with said one element temporarily removed;
   determining whether an absolute error is reduced for the candidate solution; and
   storing the absolute error associated with said one removed element.

5. The method as claimed in claim 4, further comprising the steps of:
   after storing the absolute error associated with said one removed element, iteratively:
   selecting another element of the approximation;
   calculating a second least squares candidate solution for a reduced set of elements with said other element temporarily removed;
   determining whether an absolute error is reduced for the second candidate solution; and
   storing the absolute error associated with said other removed element; and
   removing the element having the smallest absolute error if any of the stored absolute errors is less than an initial absolute error for the approximation; and
   generating a new approximation based on the reduced element set.

6. The method as claimed in claim 5, further comprising the steps of:
   prior to removing the element having the smallest absolute error if any of the stored absolute errors is less than the initial absolute error for the approximation,
   removing all elements that were detected with a negative concentration at any stage of the processing;
   generating a new approximation based on the reduced element set.

7. An electron beam system programmed to perform the method as claimed in claim 1.

8. A method of spectrum data analysis of a sample, the method comprising:
   directing an electron beam toward an unknown material;
   collecting emitted from the unknown material as a result of the electron beam impact;
   determining a spectrum of the unknown material from less than 100,000 collected x-rays;
   providing a set of data templates, each data template corresponding to a specific material;
   determining a first set of weighting factors to be applied to the data templates to approximate the spectrum, the weighting factors being determined by minimizing an error factor between the weighted element data templates and the spectrum of the unknown material;
   removing one or more of the templates having a negative weighting factor;
   re-calculating an approximation of the spectrum with said one or more data templates removed; and
   determining from the weighting factors materials present in the sample.

9. The method of claim 8 further comprising repeating the steps of removing one or more of the data templates having negative weights and re-calculating an approximation of the spectrum until there are no data templates having a negative weighting factor.

10. The method of claim 8 further comprising determining from the weighting factors and properties of the corresponding materials the relative abundance of the materials in the sample.

11. The method of claim 8 in which determining a set of first set of weighting factors to be applied to the data templates to approximate the spectrum includes determining weighting factors using a minimal residual method to minimize the error factor.

12. The method of claim 8 in which each of the data templates corresponds to an element, a mineral or a combination of elements.

13. The method of claim 8 in which collecting a spectrum of an unknown material includes collecting an x-ray spectrum using energy dispersive spectroscopy and in which the set of data templates includes the x-ray spectrum for known elements.

14. The method of claim 8 further comprising:
   substituting a pre-defined set of data templates corresponding to materials having overlapping spectral peaks for the data template of a material in the solution;

determining whether the substitution reduces the error factor; and if the substitution reduces the error factor, adjusting the weighting factors to reflect the substitution.

15. The method of claim 8 further comprising removing the data template corresponding to oxygen if the weighting factor corresponding to oxygen indicates that oxygen is present at a concentration of less than ten percent.

16. The method of claim 8 in which collecting a spectrum of an unknown material includes collecting an x-ray spectrum including less than 50,000 counts.

17. The method of claim 8 in which collecting a spectrum of an unknown material includes collecting an x-ray spectrum from an energy dispersive x-ray spectrometer in less than 100 ms.

18. The method of claim 8 further comprising:

removing the data template corresponding to a material;

recalculating the error factor; and if the error factor did not decrease, adding the data template corresponding to the material back into the data templates.

19. The method of claim 8 further comprising determining whether pre-specified pairs of elements are present and removing the element of the pair having the lesser concentration, if the concentration of that element is less than a pre-specified value.

20. The method of claim 8 further comprising determining a weight percentage of the elements present from ratios of at least one peak of each element.

21. An apparatus for determining the elemental composition of a sample, comprising:

a source of an electron beam for impinging on a sample;

an x-ray detector for detecting x-rays emitted from the sample upon impingement of the electron beam;

computer memory for:

accumulating information from the x-ray detector to determine an x-ray spectrum of the sample from less than 100,000 x-rays;

storing data templates corresponding to elements;

storing a computer program including instructions for:

determining a set of first set of weighting factors to be applied to the data templates to approximate the spectrum, the weighting factors being determined by minimizing an error factor between the weighted element data templates and the unknown spectrum;

removing one or more of the templates having a negative weighting factor in approximating the spectrum; and re-calculating an approximation of the spectrum with said one or more data templates; and a processor for executing the computer instructions to determine the composition of the sample.

22. A computer readable media comprising computer readable instructions for:

directing an electron beam toward an unknown material;

collecting less than 100,000 x-rays emitted from the unknown material as a result of the electron beam impact;

determining from the energies of the collected x-rays a spectrum of the unknown material;

determining a set of first set of weighting factors to be applied to a set of data templates to approximate the spectrum of the unknown material, the weighting factors being determined by minimizing an error factor between the element data templates weighted by the weighing factors and the spectrum of the unknown material;

removing one or more of the templates having a negative weighting factor in approximating the spectrum; and re-calculating an approximation of the spectrum with said one or more data templates.

* * * * *